(12) United States Patent
Jang

(10) Patent No.: US 11,311,497 B2
(45) Date of Patent: Apr. 26, 2022

(54) METHOD FOR SCREENING FOR DIABETES MELLITUS THERAPEUTIC AGENTS

(71) Applicant: UNIVERSITY-INDUSTRY COOPERATION GROUP OF KYUNG HEE UNIVERSITY, Yongin-si (KR)

(72) Inventor: Hyeung Jin Jang, Seoul (KR)

(73) Assignee: University—Industry Corporation Group of Kyung Hee University

( * ) Notice: Subject to any disclaimer, the term of this patent is extended or adjusted under 35 U.S.C. 154(b) by 0 days.

(21) Appl. No.: 16/657,192

(22) Filed: Oct. 18, 2019

(65) Prior Publication Data

US 2021/0069123 A1   Mar. 11, 2021

Related U.S. Application Data

(62) Division of application No. 14/908,210, filed as application No. PCT/KR2014/007141 on Aug. 1, 2014, now Pat. No. 10,493,042.

(30) Foreign Application Priority Data

Aug. 1, 2013  (KR) .................. 10-2013-0091596
Aug. 1, 2014  (KR) .................. 10-2014-0099153

(51) Int. Cl.
*A61K 31/045* (2006.01)
*A61K 9/00* (2006.01)
*G01N 33/50* (2006.01)

(52) U.S. Cl.
CPC .......... *A61K 31/045* (2013.01); *A61K 9/0043* (2013.01); *G01N 33/5008* (2013.01); *A61K 9/0053* (2013.01); *A61K 9/0073* (2013.01); *G01N 2333/605* (2013.01)

(58) Field of Classification Search
CPC ..................... G01N 33/5008; G01N 2333/605
See application file for complete search history.

(56) References Cited

U.S. PATENT DOCUMENTS

| 8,241,670 | B2 | 8/2012 | Ben-Sasson |
| 2003/0004095 | A1* | 1/2003 | Reimer .................. A23L 33/18 514/6.9 |
| 2004/0052862 | A1 | 3/2004 | Henriksen et al. |
| 2004/0202740 | A1 | 10/2004 | Tan |
| 2005/0272714 | A1 | 12/2005 | Hofmann |
| 2007/0072804 | A1 | 3/2007 | Chu et al. |
| 2011/0149816 | A1 | 6/2011 | Saito et al. |
| 2011/0257255 | A1 | 10/2011 | McLellan et al. |
| 2012/0224569 | A1 | 9/2012 | Kubota |
| 2012/0236810 | A1 | 9/2012 | Park et al. |
| 2013/0114531 | A1 | 5/2013 | Ahn et al. |

FOREIGN PATENT DOCUMENTS

| CN | 101011091 A | 8/2007 |
| CN | 101677973 A | 3/2010 |
| JP | 2004524268 A | 8/2004 |
| JP | 2005021151 A | 1/2005 |
| KR | 20070095400 A | 9/2007 |
| WO | 2004043468 A1 | 5/2004 |
| WO | 2008095297 A1 | 8/2008 |

OTHER PUBLICATIONS

Reimer et al. Endocrinology, 2001, vol. 142, pp. 4522-4528 (Year: 2001).*
Anini et al. Diabetes, 2003, vol. 52, pp. 252-259 (Year: 2003).*
Anini et al. Endocrinology, 2003, vol. 144, pp. 3244-3250 (Year: 2003).*
Lauffer et al. Diabetes, 2009, vol. 58, pp. 1058-1066 (Year: 2009).*
Mulherin et al. Endocrinology, 2011, vol. 152, pp. 4610-4619 (Year: 2011).*
Kim et al. Scientific Reports, 2017, vol. 7, No. 13978, 11 pages (Year: 2017).*
International Search Report and Written Opinion issued in counterpart PCT Application No. PCT/KR2014/007171 dated Nov. 18, 2014.

(Continued)

*Primary Examiner* — James D. Anderson
(74) *Attorney, Agent, or Firm* — Olive Law Group, PLLC; Nathan P. Letts

(57) ABSTRACT

Provided are a pharmaceutical composition including geraniol or a pharmaceutically acceptable salt thereof as an active ingredient for use in preventing or treating diabetes mellitus, and a method of preventing or treating diabetes mellitus or a complication due to diabetes mellitus of an individual, in which the method includes administering to the individual a pharmaceutical composition comprising geraniol or a pharmaceutically acceptable salt thereof as an active ingredient and inducing an olfactory stimulation to the individual using the pharmaceutical composition. Also provided is a screening method for an antidiabetic agent that may include contacting a cell expressing an olfactory receptor with a test material; measuring a level of expression of glucagon-like peptide-1 (GLP-1) secreted from the cell; and determining that the test material, when the test material promotes expression of GLP-1, as a candidate material for an antidiabetic agent. In addition, a quasi-drug composition and a cosmetic composition including geraniol for uses are provided.

6 Claims, 18 Drawing Sheets

Specification includes a Sequence Listing.

(56) References Cited

OTHER PUBLICATIONS

Mendivil et al., 2012. "Trough insulin levels in bronchoalveolar lavage following inhaled human insulin (Exubera) in patients with diabetes mellitus". Diabetes Technology & Therapeutics, vol. 14, No. 1, pp. 50-58.

Product Information for Geraniol, Sigma-Aldrich Catalog. Accessed online, Aug. 16, 2017.

Tesfaye et al. 2010. "Diabetic Neuropathies: Update on Definitions, Diagnostic criteria, Estimation of Severity, and Treatments", Diabetes Care, vol. 33, No. 10, pp. 2285-2293.

* cited by examiner

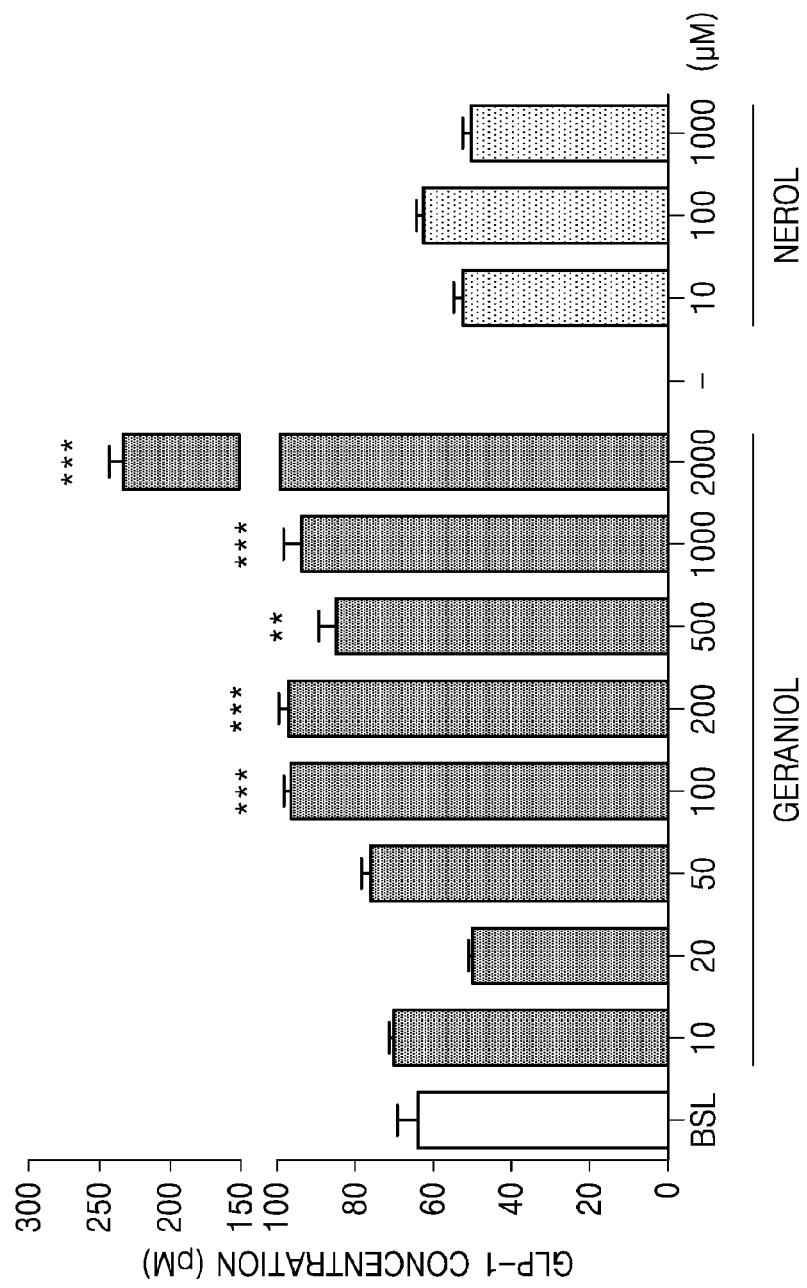

METHOD FOR SCREENING FOR DIABETES MELLITUS THERAPEUTIC AGENTS

CROSS REFERENCE TO RELATED APPLICATIONS

This application is a divisional of U.S. Ser. No. 14/908,210, filed Jan. 28, 2016 which is a § 371 U.S. National Stage of International Application PCT/KR2014/007141, filed Aug. 1, 2014, which claims the benefit of Korean Patent Appn. No. 10-2014-0099153, filed Aug. 1, 2014 and Korean Patent Appn. No. 10-2013-0091596, filed Aug. 1, 2013, the contents of which are hereby incorporated by reference in their entireties.

TECHNICAL FIELD

The present disclosure relates to a pharmaceutical composition for preventing or treating diabetes mellitus, a method for preventing or treating diabetes mellitus, and a method of screening an antidiabetic agent.

BACKGROUND OF THE DISCLOSURE

Diabetes mellitus is a disorder of glucose present in the blood discharged via the urine, which is one of chronic degenerative diseases, which is not fundamentally cured. In came into modern times, due to dietary changes and lack of exercise, a big change has occurred in an energy metabolism process, which is inherent in a human body. As a result, occurrences of chronic degenerative diseases, such as diabetes mellitus, have increased. In South Korea, it is known that the prevalence of diabetes mellitus has reached 5% to 10%, and continually increasing. In the case of the United States, the prevalence of diabetes mellitus has increased six fold over the last 40 years, due to the increase of such levels, it is expected that the number of patients will have increased to 26 million people in 2050.

The type II (insulin-independent) diabetes mellitus, which accounts for more than 95% of diabetes mellitus, is known to have two causes, namely known as a complex disorder of insulin secretion disorder and insulin resistance. In other words, diabetes mellitus is a disease that shows chronic lycemia symptoms for these complex disorders.

Insulin secretion disorder means a situation when an appropriate amount of insulin is not secreted from a beta cell of pancreas in response to the blood sugar concentration, which includes both quantitative reduction of beta cells secreting insulin and functional secretion failure. Insulin resistance means a situation when the insulin action and sensitivity is reduced at a target cell thereof, even when secreted insulin reached the target organ by the bloodstream. In general, it considered as signaling failure after binding to a cell membrane receptor. The cause thereof may be a genetic predisposition, obesity, decrease of physical activity and lycemia, or dyslipidemia. In the case of insulin resistance, a greater amount of insulin should be secreted to overcome insulin resistance; while hyperglycemia occurred due to insufficient insulin itself can worsen insulin resistance again.

Prediabetes means a blood sugar dysregulation corresponding to the previous stage of diabetes mellitus. Prediabetes refers to a high-risk group, which may be led to diabetes mellitus. A prediabetes patient has 3 to 5 times higher risk to be led to diabetes mellitus in the future than a healthy individual. In addition, although the blood sugar level of a prediabetes patient is not as high as that of diabetes mellitus patient, the blood sugar level is higher than a healthy individual, increasing blood vessel stress, thus having 3 to 5 times higher risk for cardiovascular diseases, such as stroke or myocardial infarction than in a healthy individual. Types of prediabetes may include impaired fasting lycemia (IFG), impaired glucose tolerance (IGT), or metabolic syndrome.

Olfactory receptors are mainly located in the cilia of an olfactory sensory neuron in vertebrates. In the case of insects, olfactory receptors are located in the antennae and chemosensory organ. In particular, in human and some animals, it is known that expression of olfactory receptors is found in other tissues, other than olfactory sensory neurons; however, the function of the olfactory receptors expressed in other tissues is not known clearly.

The current treatment method of diabetes mellitus may be by diet, exercise therapy, sulfonylurea, biguanide-based drugs, α-glucosidase inhibitor, or insulin. Various types of insulin developed through much research for the development of new drugs has been applied to clinically. However, these antidiabetic agents have problems that cause many side effects, such as liver dysfunction, hypoglycemia, or lacticacidemia.

Therefore, there is a need for an antidiabetic agent that decreases side effects of the conventional antidiabetic agent, improves symptoms of metabolic abnormalities, and is safe even in the case of long-term use.

SUMMARY OF THE DISCLOSURE

One aspect of the present disclosure relates to a pharmaceutical composition including geraniol or a pharmaceutically acceptable salt thereof as an active ingredient for use in preventing or treating diabetes mellitus.

One aspect of the present disclosure relates to a method of preventing or treating diabetes mellitus of an individual, wherein the method may include administering the individual with a pharmaceutical composition including geraniol or a pharmaceutically acceptable salt thereof as an active ingredient.

One aspect of the present disclosure relates to a method of preventing or treating diabetes mellitus of an individual, wherein the method may include stimulating olfaction using a pharmaceutical composition including geraniol or a pharmaceutically acceptable salt thereof as an active ingredient.

One aspect of the present disclosure relates to a screening method of an antidiabetic agent that may include contacting a cell expressing an olfactory receptor with a test material; measuring a level of expression of glucagon-like peptide-1 (GLP-1) secreted from the cell; and determining the test material, when the test material promotes expression of GLP-1, as a candidate material of an antidiabetic agent.

One aspect of the present disclosure relates to a health functional food including geraniol for use in preventing or improving diabetes mellitus.

One aspect of the present disclosure relates to a quasi-drug composition including geraniol for use in preventing or improving diabetes mellitus.

One aspect of the present disclosure relates to a cosmetic composition including geraniol for use in preventing or improving diabetes mellitus.

TECHNICAL SOLUTION

As a result of research on a function of olfactory receptor in a small intestine, it was found that an odorant stimulating olfactory receptor promotes secretion of incretin hormone by stimulating olfactory receptor in a human enteroendocrine cell and has hypoglycemic effect in a type II diabetes mellitus mouse model. Accordingly, the present disclosure was made.

An aspect of the present invention may provide a pharmaceutical composition comprising geraniol as an active ingredient for use in preventing or treating diabetes mellitus.

The term "active ingredient" includes having activity preventing or treating diabetes mellitus when the pharmaceutical composition is administered to an individual, as compared with when the pharmaceutical composition is not administered. The individual may be, for example, at least one selected from the group consisting of, a human, a mouse, a hamster, a dog, a cat, a horse, cattle, a pig, and a goat. The term "prevention" includes preventing a glucose concentration in the blood from increasing, as compared to when the pharmaceutical composition is not administered. The term "treatment" includes lowering a glucose concentration in the blood from, as compared to when the pharmaceutical composition is not administered.

The geraniol may be represented by the formula below:

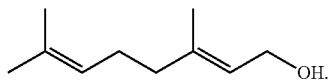

The geraniol may promote secretion of incretin hormones. Incretins are hormones secreted from a small intestine after eating, causing insulin to be released from pancreas. Recently, incretin has attracted attention as a new alternative for the treatment of diabetes mellitus. Treatment of diabetes mellitus using incretin hormones may have fewer side effects, such as hypoglycemia or a weight increase; regenerate beta cells in pancreas damaged by diabetes mellitus, and be safely used for elderly patients. Prior to development of incretins as a therapeutic agent, two important aspects of pathophysiology of diabetes mellitus were a relative insulin secretion deficiency and insulin resistance. However, in recent years, three aspects of pathophysiology of the type II diabetes mellitus are believed to further include incretin dysfunction. When orally ingested, incretins may show more powerful insulin secretion promoting action, as compared to when a glucose solution is injected intravenously. This effect is called incretin effect. Examples of incretins include glucagon-like peptide-1 (GLP-1) and glucose-dependent insulinotropic peptide (GIP). The pharmaceutical composition may be a composition for promoting secretion of GLP-1, GIP, or a combination thereof. GLP-1 may be produced mainly in cells of a small intestine, ileum and/or a large intestine. GLP-1 secretion may be stimulated physiologically in conjunction with foods, such as fat and carbohydrates. GLP-1 may act directly on beta cells in pancreas, stimulate the proliferation and differentiation of the beta cells, thus increasing increase secretion and synthesis of insulin. In addition, GLP-1 may also suppress intestinal motility and secretion of gastric juice and pancreatic juice.

A cell that secretes gastrin, ghrelin, a glucose-dependent insulinotropic peptide (GIP), secretin, and/or cholecystokinin (CCK) may present in a stomach and a proximal small intestine. A cell that secretes glucagon-like-peptide-1 (GLP-1), glucagon-like-peptide-2 (GLP-2), peptide YY, and/or neurotensin may present in an ileum and a large intestine. GLP-1 may be produced mainly in cells of a small intestine, ileum and/or a large intestine. GLP-1 secretion may be stimulated physiologically in conjunction with foods, such as fat and carbohydrates. GLP-1 may act directly on beta cells in pancreas, stimulate the proliferation and differentiation of beta cells, thus increasing increase secretion and synthesis of insulin. In addition, GLP-1 may also suppress intestinal motility and secretion of gastric juice and pancreatic juice.

Furthermore, the pharmaceutical composition may be for stimulating cell expressing olfactory receptor or an olfactory receptor. The cell expressing olfactory receptor may be an olfactory cell or an enteroendocrine cell.

The olfactory cell may include sensory cells excluding supporting cells in charge of supporting cells constituting olfactory epithelium and basal cells. The enteroendocrine cell may be specialized endocrine cells of gastrointestinal tract or pancreas. The olfactory receptor may be a human olfactory receptor. The human olfactory receptor may include a human olfactory receptor OR1A1 or OR1G1. The olfactory receptor will be described below.

The enteroendocrine cell may produce gastrointestinal hormones or peptides in response to various stimulations and release gastrointestinal hormones or peptides into a blood vessel for systemic effect. A cell that secretes gastrin, ghrelin, GIP, secretin, and/or CCK may present in a stomach and a proximal small intestine. A cell that secretes GLP-1, GLP-2, peptide YY, and/or neurotensin may present in an ileum and a large intestine.

The geraniol may be an odorant. The geraniol may be included in a pharmaceutical composition alone or in a combination.

The pharmaceutical composition according to the present disclosure may be a formulation for parenteral or oral administration. In addition, a preparation for parenteral administration of the pharmaceutical composition may be a formulation for administration by inhalation. The pharmaceutical composition may be administered by inhalation via a nasal cavity or oral routes. The pharmaceutical composition may be administered in the form that may stimulate olfactory stimulation, e.g., olfactory cells. The inhalation may stimulate olfactory cells in a nasal cavity. The inhalation may be smelling. The smelling may include stimulating olfactory cells in a nasal cavity prior to passing a pulmonary route or without passing a pulmonary route. The smelling may be smelling a smell of a material. The smelling may mean smelling a smell or aroma of a material in a degree suitable for stimulating olfactory cells in a nasal cavity.

The formulation for administration by inhalation may be an aerosol formulation including a propellant or not. The preparation may be administered in spray form. The pharmaceutical composition may be administered in spray form to a nasal cavity. The pharmaceutical composition may be administered using a dry powder inhaler, a compression weighing dose inhaler, or a spray.

The pharmaceutical composition may be prepared in dried powder form. The dried powder form may include lactose, dextran, mannitol, or glucose. The dried powder form may further include a diluent or a carrier.

The pharmaceutical composition may be a composition for intranasal administration or a composition for nasal transfer. The pharmaceutical composition may be in any suitable form for nasal transfer. The suitable form may include an aqueous solution or a non-aqueous solution or powder.

The pharmaceutical composition may be an odorant. The odorant may be a material having a certain smell. In addition, the odorant may include at least one selected from the group consisting of an alcohol, an acid, pyrazine, an aldehyde, a ketone, an ester, a sulfuric compound, and a lactone.

For example, the odorant may include an alcohol, such as 1-hexanol, 2-ethyl-1-hexanol, 1-heptanol, 1-octanol, 2-octanol, 3-octanol, 4-octanol, 1-nonanol, 2-nonanol, 1-decanol, 1-dodecanol, geraniol, geranylgeraniol, phenyl metanol, mentol, thymol, guaiacol, maltol, nerol, phenol, isoeugenol, eugenol, and/or bourgeonal. The odorant may also include an acid, such as propionic acid, isobutyric acid, butyric acid, hexanoic acid, heptanoic acid, octanoic acid, nonanoic acid, decanoic acid, dodecanoic acid, and/or isovaleric acid. The odorant may also include pyrazine, such as 2-methyl pyrazine, and/or 2-isobutyl-3-methoxy pyrazine. The odorant may also include an aldehyde, such as hexanal, heptanal, octanal, nonanal, decanal, undecanal, dodecanal, benzaldehyde, lyral, (+/−) citronellal, cinnamaldehyde, helional, para-anisaldehyde, vanillin, and/or ethyl-vanillin. The odorant may also include a ketone, such as 2-heptanone, 2-octanone, 3-octanone, 2-nonanone, 3-nonanone, 2-decanone, 2-dodecanone, 3-hydrixybutan-2-one, 6-methyl-5-hepten-2-one, piperonyl acetone, menthone, beta-ionone, cyclohexanone, acetophenone, hedione, and/or camphor. The odorant may also include an ester, such as iso-amyl acetate, ethyl butyrate, ethyl isobutyrate, butyl butyrate, ethyl hexanoate, ethyl heptanoate, ethyl octanoate, ethyl nonanoate, ethyl decanoate, methyl hexanoate, methyl heptanoate, methyl octanoate, methyl nonanoate, methyl decanoate, methyl salicylate, and/or geranyl acetate. The odorant may also include a sulfuric compound, such as dimethyl disulfide, S-methyl thiobutanoate, thiazol, and/or benzothiazol. The odorant may also include a lactone, such as coumarin and/or gamma-decalactone. The odorant may also include other pyridine, quinoline, indol, anisol, trans-anethol, cineol, estragol, safrol, citralva, and/or limonene.

The pharmaceutical composition according to the present disclosure may further include an excipient including a diluent, a lubricant, a granulating agent, a flow improver, or a coloring agent.

A formulation for oral administration may be a tablet, granules, a capsule, or powder formulation. In the case of preparation for oral administration, a diluent or an excipient, e.g., a filler, an extender, a binder, a humectant, a disintergrant, and a surfactant may be used in the preparation.

A solid preparation for oral administration may be prepared by mixing a tablet, a pill, powder, granules, and a capsule. In addition to simple excipients, lubricants, such as magnesium stearate talc. A liquid preparation for oral administration may include a suspension, an oral solution, an emulsion, and syrup and further include various excipients, e.g., a humectant, a sweetener, a flavoring agent, and a preservative, in addition to simple diluents, e.g., water and liquid paraffin, which are generally used. A formulation for oral administration may include an active ingredient of about 0.1 to 1000 mg per kilogram of body weight, 0.1 to 800 mg per kilogram of body weight, 1 to 500 mg per kilogram of body weight, or 100 to 300 mg per kilogram of body weight at a dosage unit. The formulation for oral administration may be administered one to six times a day, two to five times a day, or three to four times a day.

The pharmaceutical composition according to the present disclosure may be used alone for preventing and treating diabetes mellitus. Alternatively, the pharmaceutical composition may be used in combination with surgery, radiation treatment, hormone therapy, chemotherapy, aromatherapy, and/or a method using biological response modifier.

Desirable dosage of the pharmaceutical composition according to the present disclosure may vary depending on the status and weight of a patient, degree of disease, form of a drug, administration routes and period. Accordingly, one of ordinary skill in the art may properly select the dosage. The pharmaceutical composition may be administered in an amount of 0.0001 mg/kg to 10000 mg/kg a day. The composition may be administered once a day or several times a day.

Another aspect of the present disclosure provides a health functional food for use in preventing or improving diabetes mellitus including a screened compound, e.g., geraniol, which is described herein. The term 'health functional food' may refer to food having a biological regulation function, such as preventing or improving disease, biophylaxis, immunity, recovery from illness, and aging suppression. A health functional food may be harmless in the case of taking for a long-term. A health functional food may include functional beverage, a baking product, a snack bar, a candy, a nutritional bar, a processed food, an oil product, a dairy product, or a frozen food.

The functional beverage may further include various flavoring agents or natural carbohydrates. The natural carbohydrates may be monosaccharides, e.g., glucose or fructose, disaccharides, e.g., maltose or sucrose, a natural sweetener, e.g., dextrin or cyclodextrin, and a synthetic sweetener, e.g., saccharin or aspartame. The natural carbohydrates may be included in a range of about 0.01 g to 10 g or about 0.01 g to 0.1 g per 100 ml of the pharmaceutical composition according to the present disclosure.

The health functional food may further include additives, such as a nutritional supplement, vitamins, an electrolyte, a flavoring agent, a coloring agent, pectic acid and a salt thereof, alginic acid and a salt thereof, an organic acid, a protective colloid thickener, a PH adjuster, a stabilizer, a preservative, glycerin, alcohol, or a carbonating agent used for a carbonated drink. A screened compound or a pharmaceutically acceptable salt thereof described herein, e.g., geraniol, may be included in the health functional food in a range of about 0.1 weight percent (wt %) to 15 wt %, about 1 wt % to 10 wt %, or about 5 wt % to 10 wt %.

According to another aspect of the present disclosure, provided is a method of preventing or treating diabetes mellitus or a complication due to diabetes mellitus of an individual, wherein the method may include administering the individual with a pharmaceutical composition including a screened compound, e.g., geraniol, which is described herein, or a pharmaceutically acceptable salt thereof as an active ingredient.

In the method, the term "individual" refers to an individual in need of treatment of a disease. The individual may be a patient suffering from diabetes mellitus or an individual who have been diagnosed with diabetes mellitus. The individual may be mammalia, for example, at least one selected from the group consisting of a human or non-human primates, a mouse, a rat, a dog, a cat, a horse, and cattle.

The diabetes mellitus may be type II diabetes mellitus, type I diabetes mellitus, prediabetes, or a combination thereof.

The complication due to diabetes mellitus may include at least one selected from the group consisting of a cardiovascular disorder, neuropathy, skin infection, microangiopathy, skin symptoms of hypersensitivity reaction by treatment drug, clouding of the lens and cataract, diabetic retinopathy, diabetic nephropathy, and diabetic neuropathy.

The administering may be for stimulating olfactory stimulation, e.g., olfactory cells of a subject. The administering may be a parenteral administration or an oral administration. The administering may be by inhalation via a nasal cavity or oral routes. The inhalation may stimulate olfactory cells in a nasal cavity. The inhalation may be smelling. The smelling may include stimulating olfactory cells in a nasal cavity prior to passing a pulmonary route or without passing a pulmonary route. The smelling may be smelling a smell of a material. The smelling may mean smelling a smell or aroma of a material in a degree suitable for stimulating olfactory cells in a nasal cavity.

The method of treating may be aromatherapy. The aromatherapy may also be called as aroma therapy. The aromatherapy may be stimulating olfactory cells, which may be performed by smelling.

For preventing and treating diabetes mellitus, the method may be used alone or in combination with aromatherapy, surgery, radiation treatment, hormone therapy, chemotherapy, and a method using biological response modifier.

Another aspect of the present disclosure provides a screening method of an antidiabetic agent that may include contacting a cell expressing an olfactory receptor with a test material; measuring a level of expression of GLP-1 secreted from the cell; and determining the test material, when the test material promotes expression of GLP-1, as a candidate material of an antidiabetic agent.

In the contacting of a cell expressing an olfactory receptor with a test material, the olfactory receptor is a receptor that may sense odor molecules expressed from the outside of a cell membrane of an olfactory sensory neuron. When a certain olfactory receptor is stimulated by odor molecules, signal transduction may begin in an olfactory sensory neuron, this stimulation may be delivered to a limbic area of a brain. An olfactory receptor is a G protein-coupled receptor (GPCR), and 900 or more types thereof may be expressed from human genome, which is equivalent to three percent of human genes.

In a mechanism in an olfactory sensory neuron of an olfactory receptor, when odor molecules bind to an olfactory receptor, the olfactory receptor may undergo a structural change. Olfactory related G proteins in an olfactory sensory neuron, e.g., G protein alpha-subunit, olfactory type, and/or Golf may be activated, starting the mechanism. Such a structural change of an olfactory receptor may activate adenylate cyclase (AC) so as to change ATP to cyclic AMP (cAMP). The increased cAMP in a cell may open a cyclic nucleotide-gated ion channel (CNG-channel), inducing calcium and sodium ions to flow into the cell. As a result, depolarization of the olfactory sensory neuron may be induced, transmitting an action potential to a brain.

The olfactory receptor may be a human olfactory receptor. The human olfactory receptor may include a human olfactory receptor OR1A1 (ORL512; senselab.med.yale.edu/odordb/eavData.aspx?db=5&c1=22&o=1912)or OR1G1 (ORL3747; senselab.med.yale.edu/_sitenet/eavObList.aspx?db=4&c1=22&at=36&vid=14668). A list of human olfactory receptors by Senomyx is shown in the table below.

TABLE 1

| No. | Olfactory receptor |
|---|---|
| 1 | ORL3001 |
| 2 | ORL3002 |
| 3 | ORL3003 |
| 4 | ORL3004 |
| 5 | ORL3005 |
| 6 | ORL3006 |
| 7 | ORL3007 |
| 8 | ORL3008 |
| 9 | ORL3009 |
| 10 | ORL3010 |
| 11 | ORL3011 |
| 12 | ORL3012 |
| 13 | ORL3013 |
| 14 | ORL3014 |
| 15 | ORL3015 |
| 16 | ORL3016 |
| 17 | ORL3017 |
| 18 | ORL3018 |
| 19 | ORL3019 |
| 20 | ORL3020 |
| 21 | ORL3023 |
| 22 | ORL3024 |
| 23 | ORL3025 |
| 24 | ORL3026 |
| 25 | ORL3027 |
| 26 | ORL3028 |
| 27 | ORL3029 |
| 28 | ORL3030 |
| 29 | ORL3031 |
| 30 | ORL3032 |
| 31 | ORL3044 |
| 32 | ORL3045 |
| 33 | ORL3046 |
| 34 | ORL3047 |
| 35 | ORL3048 |
| 36 | ORL3049 |
| 37 | ORL3050 |
| 38 | ORL3051 |
| 39 | ORL3052 |
| 40 | ORL3053 |
| 41 | ORL3054 |
| 42 | ORL3093 |
| 43 | ORL3094 |
| 44 | ORL3095 |
| 45 | ORL3131 |
| 46 | ORL3132 |
| 47 | ORL3137 |
| 48 | ORL3138 |
| 49 | ORL3139 |
| 50 | ORL3140 |
| 51 | ORL3141 |
| 52 | ORL3142 |
| 53 | ORL3143 |
| 54 | ORL3144 |
| 55 | ORL3148 |
| 56 | ORL3171 |
| 57 | ORL3172 |
| 58 | ORL3173 |
| 59 | ORL3174 |
| 60 | ORL3175 |
| 61 | ORL3176 |
| 62 | ORL3177 |
| 63 | ORL3178 |
| 64 | ORL3179 |
| 65 | ORL3216 |
| 66 | ORL3217 |
| 67 | ORL3218 |
| 68 | ORL3219 |
| 69 | ORL3220 |
| 70 | ORL3221 |
| 71 | ORL3222 |
| 72 | ORL3223 |
| 73 | ORL3224 |
| 74 | ORL3225 |
| 75 | ORL3226 |
| 76 | ORL3227 |
| 77 | ORL3228 |
| 78 | ORL3229 |
| 79 | ORL3231 |
| 80 | ORL3232 |
| 81 | ORL3233 |
| 82 | ORL3234 |
| 83 | ORL3235 |
| 84 | ORL3236 |
| 85 | ORL3237 |
| 86 | ORL3238 |

TABLE 1-continued

| No. | Olfactory receptor |
|---|---|
| 87 | ORL3239 |
| 88 | ORL3247 |
| 89 | ORL3265 |
| 90 | ORL3274 |
| 91 | ORL3275 |
| 92 | ORL3276 |
| 93 | ORL3277 |
| 94 | ORL3278 |
| 95 | ORL3279 |
| 96 | ORL3280 |
| 97 | ORL3281 |
| 98 | ORL3282 |
| 99 | ORL3283 |
| 100 | ORL3284 |
| 101 | ORL3285 |
| 102 | ORL3286 |
| 103 | ORL3287 |
| 104 | ORL3288 |
| 105 | ORL3289 |
| 106 | ORL3290 |
| 107 | ORL3291 |
| 108 | ORL3292 |
| 109 | ORL3293 |
| 110 | ORL3294 |
| 111 | ORL3295 |
| 112 | ORL3296 |
| 113 | ORL3297 |
| 114 | ORL3298 |
| 115 | ORL3299 |
| 116 | ORL3300 |
| 117 | ORL3301 |
| 118 | ORL3302 |
| 119 | ORL3303 |
| 120 | ORL3304 |
| 121 | ORL3305 |
| 122 | ORL3306 |
| 123 | ORL3307 |
| 124 | ORL3308 |
| 125 | ORL3309 |
| 126 | ORL3310 |
| 127 | ORL3311 |
| 128 | ORL3312 |
| 129 | ORL3313 |
| 130 | ORL3314 |
| 131 | ORL3315 |
| 132 | ORL3316 |
| 133 | ORL3317 |
| 134 | ORL3318 |
| 135 | ORL3319 |
| 136 | ORL3320 |
| 137 | ORL3321 |
| 138 | ORL3322 |
| 139 | ORL3323 |
| 140 | ORL3324 |
| 141 | ORL3325 |
| 142 | ORL3326 |
| 143 | ORL3327 |
| 144 | ORL3328 |
| 145 | ORL3329 |
| 146 | ORL3330 |
| 147 | ORL3331 |
| 148 | ORL3332 |
| 149 | ORL3333 |
| 150 | ORL3334 |
| 151 | ORL3335 |
| 152 | ORL3336 |
| 153 | ORL3337 |
| 154 | ORL3338 |
| 155 | ORL3339 |
| 156 | ORL3340 |
| 157 | ORL3342 |
| 158 | ORL3343 |
| 159 | ORL3344 |
| 160 | ORL3345 |
| 161 | ORL3346 |
| 162 | ORL3347 |
| 163 | ORL3348 |
| 164 | ORL3349 |
| 165 | ORL3350 |
| 166 | ORL3351 |
| 167 | ORL3352 |
| 168 | ORL3353 |
| 169 | ORL3354 |
| 170 | ORL3355 |
| 171 | ORL3356 |
| 172 | ORL3357 |
| 173 | ORL3358 |
| 174 | ORL3359 |
| 175 | ORL3360 |
| 176 | ORL3361 |
| 177 | ORL3362 |
| 178 | ORL3363 |
| 179 | ORL3364 |
| 180 | ORL3365 |
| 181 | ORL3366 |
| 182 | ORL3367 |
| 183 | ORL3368 |
| 184 | ORL3369 |
| 185 | ORL3370 |
| 186 | ORL3371 |
| 187 | ORL3372 |
| 188 | ORL3373 |
| 189 | ORL3374 |
| 190 | ORL3375 |
| 191 | ORL3376 |
| 192 | ORL3377 |
| 193 | ORL3378 |
| 194 | ORL3379 |
| 195 | ORL3380 |
| 196 | ORL3381 |
| 197 | ORL3382 |
| 198 | ORL3383 |
| 199 | ORL3384 |
| 200 | ORL3385 |
| 201 | ORL3386 |
| 202 | ORL3387 |
| 203 | ORL3388 |
| 204 | ORL3389 |
| 205 | ORL3390 |
| 206 | ORL3391 |
| 207 | ORL3392 |
| 208 | ORL3393 |
| 209 | ORL3394 |
| 210 | ORL3395 |
| 211 | ORL3396 |
| 212 | ORL3397 |
| 213 | ORL3398 |
| 214 | ORL3399 |
| 215 | ORL3400 |
| 216 | ORL3401 |
| 217 | ORL3402 |
| 218 | ORL3403 |
| 219 | ORL3404 |
| 220 | ORL3405 |
| 221 | ORL3406 |
| 222 | ORL3407 |
| 223 | ORL3408 |
| 224 | ORL3409 |
| 225 | ORL3410 |
| 226 | ORL3411 |
| 227 | ORL3412 |
| 228 | ORL3413 |
| 229 | ORL3414 |
| 230 | ORL3415 |
| 231 | ORL3416 |
| 232 | ORL3417 |
| 233 | ORL3418 |
| 234 | ORL3419 |
| 235 | ORL3420 |
| 236 | ORL3421 |
| 237 | ORL3422 |
| 238 | ORL3423 |
| 239 | ORL3424 |
| 240 | ORL3425 |

TABLE 1-continued

| No. | Olfactory receptor |
|---|---|
| 241 | ORL3426 |
| 242 | ORL3427 |
| 243 | ORL3428 |
| 244 | ORL3429 |
| 245 | ORL3430 |
| 246 | ORL3431 |
| 247 | ORL3432 |
| 248 | ORL3433 |
| 249 | ORL3434 |
| 250 | ORL3435 |
| 251 | ORL3436 |
| 252 | ORL3438 |
| 253 | ORL3457 |
| 254 | ORL3458 |
| 255 | ORL3459 |
| 256 | ORL3460 |
| 257 | ORL3461 |
| 258 | ORL3462 |
| 259 | ORL3463 |
| 260 | ORL3464 |
| 261 | ORL3465 |
| 262 | ORL3466 |
| 263 | ORL3467 |
| 264 | ORL3468 |
| 265 | ORL3469 |
| 266 | ORL3470 |
| 267 | ORL3655 |
| 268 | ORL3656 |
| 269 | ORL3657 |
| 270 | ORL3658 |
| 271 | ORL3661 |
| 272 | ORL3662 |
| 273 | ORL3663 |
| 274 | ORL3681 |
| 275 | ORL3682 |
| 276 | ORL3683 |
| 277 | ORL3684 |
| 278 | ORL3685 |
| 279 | ORL3686 |
| 280 | ORL3687 |
| 281 | ORL3688 |
| 282 | ORL3689 |
| 283 | ORL3690 |
| 284 | ORL3691 |
| 285 | ORL3692 |
| 286 | ORL3693 |
| 287 | ORL3694 |
| 288 | ORL3695 |
| 289 | ORL3697 |
| 290 | ORL3698 |
| 291 | ORL3699 |
| 292 | ORL3700 |
| 293 | ORL3721 |
| 294 | ORL3722 |
| 295 | ORL3723 |
| 296 | ORL3725 |
| 297 | ORL3736 |
| 298 | ORL3737 |
| 299 | ORL3738 |
| 300 | ORL3745 |
| 301 | ORL3746 |
| 302 | ORL3747 |
| 303 | ORL3748 |
| 304 | ORL3760 |
| 305 | ORL3761 |
| 306 | ORL3762 |
| 307 | ORL3763 |
| 308 | ORL3764 |
| 309 | ORL3765 |
| 310 | ORL3766 |
| 311 | ORL3767 |
| 312 | ORL3768 |
| 313 | ORL3769 |
| 314 | ORL3774 |
| 315 | ORL3775 |
| 316 | ORL3802 |
| 317 | ORL3803 |
| 318 | ORL4124 |
| 319 | ORL4126 |
| 320 | ORL4127 |

The cell expressing olfactory receptor may be an olfactory cell or an enteroendocrine cell. The olfactory cell and enteroendocrine cell are the same as defined herein.

A test material in the present disclosure may be an unidentified material used in screening for testing if stimulation of an olfactory receptor promotes GLP-1 secretion. The test material may be a monoterpenoid, such as geraniol. The test material may include geraniol, linalool, citronella, citronellol, or citral. The test material may be an odorant.

The contacting of a cell expressing an olfactory receptor with a test material may be carried out using one or more methods, e.g., incubating a cell with a test material in a liquid medium or contacting a fixed solid support of a test material with a cell.

After contacting a cell expressing olfactory receptor with the test material, and then, the cell may be cultured for about 1 hour or more, about 1 to 48 hours, 24 to 48 hours, or 36 to 48 hours. For about 1 to 120 minutes, a cell expressing olfactory receptor may be incubated with the test material at a concentration of about 0.1 to 2000 μM, about 10 to 2000 μM, about 100 to 1500 μM, or about 500 to 1000 μM.

A screening method of an antidiabetic agent may include measuring a level of expression of GLP-1 secreted from a cell. In the measuring of a level of expression of GLP-1 secreted from the cell, after contacting a cell expressing olfactory receptor with a test material, the GLP-1 secretion amount may be measured by enzyme-linked immunosorbent assay (ELISA), multiplex (GLP-1 multiplex assay), radioimmunoassay, immunofluorescence (fluorescent antibody method), or latex agglutination, thereby identifying the increase of the GLP-1 secretion amount. In addition, increase of expression of GLP-1 may be identified using one or more methods, such as a method of measuring the amount of mRNA of GLP-1 or other methods of measuring the level of expression of GLP-1.

The screening method of an antidiabetic agent may include determining a test material as an antidiabetic agent when the test material promotes expression of GLP-1. In the determining of a test material as an antidiabetic agent when the test material promotes expression of GLP-1, in the case that the GLP-1 secretion amount is increased, as compared with the case that the treatment of the test material is not used, the test material may be determined to promote GLP-1 secretion.

A test material promoting GLP-1 secretion may be a candidate material of an antidiabetic agent. Diabetes mellitus may include type II diabetes mellitus, type I diabetes mellitus, and/or prediabetes. Type II diabetes mellitus may be induced by a complex disorder of a secretion disorder of insulin and/or insulin resistance. Prediabetes may include symptoms, such as impaired fasting lycemia (IFG), impaired glucose tolerance (IGT), or metabolic syndrome.

According to another aspect of the present disclosure, provided is a pharmaceutical composition for preventing or treating diabetes mellitus, which includes a screened compound or a pharmaceutically acceptable salt thereof as an active ingredient. The screened compound may be a monoterpenoid. The screened compound may include geraniol, linalool, citronella, citronellol, or citral.

According to another aspect of the present disclosure, provided is a quasi-drug composition for preventing or improving diabetes mellitus, including geraniol or the screened compound as an active ingredient.

The geraniol and screened compound are the same as described herein. In greater detail, the pharmaceutical composition of the present invention may be added to a quasi-drug composition for preventing or improving diabetes mellitus.

The term "quasi-drug" refers to an article made from fiber, rubber, or similar materials used in humans or animals for the purpose of curing, alleviating, treating, or preventing diseases; articles, other than instruments, machines or the like, which have a mild action on or have no direct influence on the human body; and articles, falling within the range of agents used to sterilize, kill insects and for similar purposes. All of the articles exclude those intended at the same time to be prescribed to diagnosing, curing, alleviating, treating or preventing diseases in humans or animals other than instruments, machines or the like, and for pharmaceutically affecting the structure and function of humans or animals other than instruments, machines or the like. The quasi-drug may further include a skin external agent and a personal hygiene product.

When the geraniol is added to a quasi-drug composition for preventing or improving diabetes mellitus, the geraniol itself may be added thereto or used in combination with other quasi-drug components. The geraniol may be properly used based on a common method. The mixture amount of the active ingredient may be appropriately determined, depending on the purpose of the use (prevention, health, or treatment).

The quasi-drug composition may include, not particularly limited to, a personal hygiene product, a skin external agent, a disinfection cleaner, a shower foam, a mouthwash, a wet tissue, a detergent soap, a hand wash, a humidifier filler, a mask, an ointment, or a filter filler. The skin external agent may be manufactured, not particularly limited to, preferably, as an ointment, a lotion, a spray, a patch, a cream, powder, a suspension, a gel agent, or a form of gel. The personal hygiene product may be soap, a wet tissue, a tissue, a shampoo, a toothpaste, a hair care product, an air freshener gel, or a wash gel.

According to another aspect of the present disclosure, provided is a cosmetic composition for use in preventing or improving diabetes mellitus, including geraniol or the screened compound as an active ingredient. The geraniol and diabetes mellitus are the same as described herein.

The geraniol or screened compound may be included, as in the pharmaceutical composition, in the cosmetic composition in an amount of 0.1 wt % to 20 wt %, e.g., 0.1 wt % to 5 wt %, 0.4 to 0.6 wt %, or 0.5 wt %, based on the total weight of the cosmetic composition.

The cosmetic composition may include components that are commercially used a cosmetic composition other than geraniol, for example, at least one additive selected from the group consisting of water, a surfactant, a humectant, a lower alcohol, a chelate agent, a sterilizer, an antioxidant, a preservative, a pigment, and perfume.

In addition, the cosmetic composition may be prepared in any suitable formulation commercially manufactured. For example, the cosmetic composition may be formulated in a solution, an emulsion, a suspension, a paste, a cream, a lotion, a gel, powder, a spray, a surfactant-containing cleansing, oil, a soap, a liquid cleanser, a bath agent, foundation, makeup base, essence, beauty wash, foam, a pack, skin lotion, a sunscreen cream, or sun oil.

In the case that the formulation of the cosmetic composition is powder or spray, lactose, talc, silica, aluminum hydroxide, calcium silicate, or polyamide powder may be used as a carrier ingredient, and in particular, when the formulation is spray, the formulation may further include a propellant, such as chloro fluoro hydrocarbon, propane/butane, or dimethyl ether.

When the formulation of the cosmetic composition is solution or emulsion, as a carrier ingredient, a solvent, a solubilizer or an emulsifier, e.g., water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester, may be used.

When the formulation of the cosmetic composition is suspension, as a carrier ingredient, a liquid diluent, e.g., such as water, ethanol, or propylene glycol, a suspension, e.g., ethoxylated isostearyl alcohol, poly-oxyethylene sorbitol ester, and poly oxy ethylene sorbitan ester, microcrystalline cellulose, aluminum metahydroxide, bentonite, or tragacanth, may be used.

When the formulation of the cosmetic composition is paste, cream, or gel, as a carrier ingredient, animal oil, vegetable oil, wax, paraffin, starch, tragacanth, a cellulose derivative, polyethylene glycol, silicon, bentonite, silica, talc, or zinc oxide, may be used.

When the formulation of the cosmetic composition is a surfactant-containing cleansing, as a carrier ingredient, aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkyl amido betaine, aliphatic alcohol, fatty acid glyceride, fatty acid diethanolamide, vegetable oil, a lanolin derivative, or ethoxylated glycerol fatty acid ester may be used.

In addition, components included in the cosmetic composition may be the same amount as those commonly used in the skin science field.

Advantageous Effects

A pharmaceutical composition according to one aspect of the present disclosure may promote secretion of GLP-1, i.e., an incretin hormone, in a human enteroendocrine cell and have hypoglycemic effect in a diabetes mellitus mouse model. Thus, diabetes mellitus may be effectively prevented or treated using the pharmaceutical composition. In addition, a pharmaceutical composition of a formulation for administration by inhalation may be an alternative of a formulation for oral administration, and thus the pharmaceutical composition may be administered to an individual to minimize the burden on the liver. Furthermore, the pharmaceutical composition may bring hypoglycemic effect in a glucose concentration in the blood dependently.

A method of preventing or treating diabetes mellitus of an individual according to one aspect of the present disclosure may effectively prevent or treat diabetes mellitus.

A screening method according to one aspect of the present disclosure may stimulate an olfactory receptor and effectively screen a compound promoting GLP-1 secretion.

A health functional food aspect according to one aspect of the present disclosure may bring hypoglycemic effect in a glucose concentration in the blood dependently, thus effectively preventing or improving diabetes mellitus.

A quasi-drug composition aspect according to one aspect of the present disclosure may bring hypoglycemic effect in a glucose concentration in the blood dependently, thus effectively preventing or improving diabetes mellitus.

A cosmetic composition aspect according to one aspect of the present disclosure may bring hypoglycemic effect in a glucose concentration in the blood dependently, thus effectively preventing or improving diabetes mellitus.

BRIEF DESCRIPTION OF THE DRAWINGS

FIG. 1A is a result of verification of GLP-1 secretion promoting effect by geraniol in a NCI-H716 cell, i.e., a human enteroendocrine cell. It was found that geraniol dose-dependently promotes GLP-1 secretion in a human enteroendocrine cell, as compared with the isomer thereof, nerol.

FIG. 4 is a graph of measurement of change amount of cAMP after 10 minutes elapsed from 10 μM forskolin treatment. Forskolin treatment was found to show a similar pattern as the geraniol treatment.

FIG. 7A A to C are results that verify GLP-1 co-expression with OR1A1 (olfactory receptor family 1 subfamily A member 1) or OR1G1 in an ileum tissue of a human through immunofluorescent staining. FIG. 7A D to F are results that verify expression of GLP-1 and OR1A1, OR1G1, or Golf (G protein, olfactory type) in an NCI-H716 cell, i.e., a human enteroendocrine cell.

FIG. 7B G to I are results that verify GLP-1 co-expression with olfactory marker protein (OMP), OR1G1, or OR1A1 in duodenum and ileum tissues of a mouse. FIG. 7B G is for illustrating expressions of GLP-1, OR1A1, and OR1G1 through immunofluorescent staining, in an order from the left to the right.

DETAILED DESCRIPTION OF THE DISCLOSURE

The present invention will be described in further detail with reference to the following examples. However, the description is for understanding the present invention only and is not intended to limit the scope of the present invention.

EXAMPLE 1

GLP-1 Secretion Promotion in Enteroendocrine Cell by Geraniol, and Changes of cAMP (1) Verification of GLP-1 Secretion Promotion in Enteroendocrine Cell by Geraniol 1-1. Cell Culture A NCI-H716 cell, i.e., a human enteroendocrine cell, was obtained from Korean Cell Line Bank. The obtained cell was culture in RPMI 1640 medium until the number of obtained cells increased in a proper amount. Then, the cells were moved to a matrigel-coated plate, and then cultured in DMEM medium for 48 hours, for endocrine differentiation.

1-2. Preparation of Test Material

Geraniol and nerol were purchased from Signa-Aldrich, USA.

1-3. Treatment of Cell with Test Material

Human enteroendocrine cells were each treated with geraniol at a concentration of 10, 20, 50, 100, 200, 500, 1000, and 2000 μM, respectively, and then cells were cultured for 1 hour. A human enteroendocrine cell was treated with nerol, which is an isomer of geraniol, as a comparison group, i.e., a negative control group, under the same condition as in the treating with geraniol.

1-4. Analysis of GLP-1 secretion amount

GLP-1 secretion from the cell treated with geraniol and the cell treated with nerol were identified using enzyme-linked immunosorbent assay (ELISA). ELISA was carried out using a GLP-1 ELISA kit, available from Millipore, based on the user manual. The amount of GLP-1 secretion was measured using a fluoroskan ascent microplate reader (Thermo Electron Corp., Finland).

FIG. 1A is a result of verification of GLP-1 secretion promoting effect by geraniol in a NCI-H716 cell, i.e., a human enteroendocrine cell. It was found that geraniol dose-dependently promotes GLP-1 secretion in a human enteroendocrine cell, as compared with nerol, i.e., the isomer thereof. As shown in FIG. 1A, it was found that geraniol promoted GLP-1 secretion in proportion to the treatment amount of geraniol in a human enteroendocrine cell. However, the treatment of nerol, i.e., an isomer thereof, had no GLP-1 secretion promotion effect.

(2) Analysis of GLP-1 Secretion by Geraniol in Enteroendocrine Cell in which Olfactory Receptor is Knocked-Down In a human enteroendocrine cell, in which an olfactory receptor is knocked-down by small-interference RNA (siRNA), an olfactory receptor signal transduction mechanism was identified.

Human enteroendocrine cells in which olfactory receptors OR1A1 and OR1G1 were knocked-down by siRNAs, respectively, were cultured. SiRNAs for knocking-down OR1A1 (SEQ ID NO. 1 and 2, siRNA No. 1108058) and OR1G1 (SEQ ID NO. 3 and 4, siRNA No. 1108121) are available from Bioneer Co. (South Korea). Lipofectamine 2000 (available from Life technology, USA) was used to carry out intracellular transfection, based on the user manual.

Figure 1B:
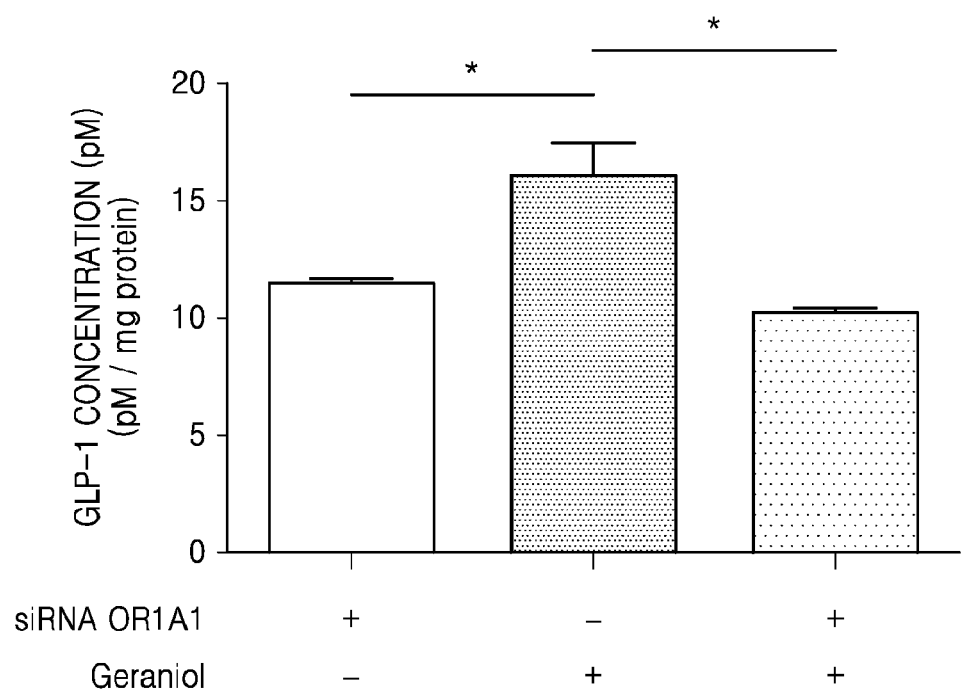
FIG. 1B is a graph showing that geraniol stimulates an olfactory receptor, OR1A1, promoting GLP-1 secretion.
Figure 1C:
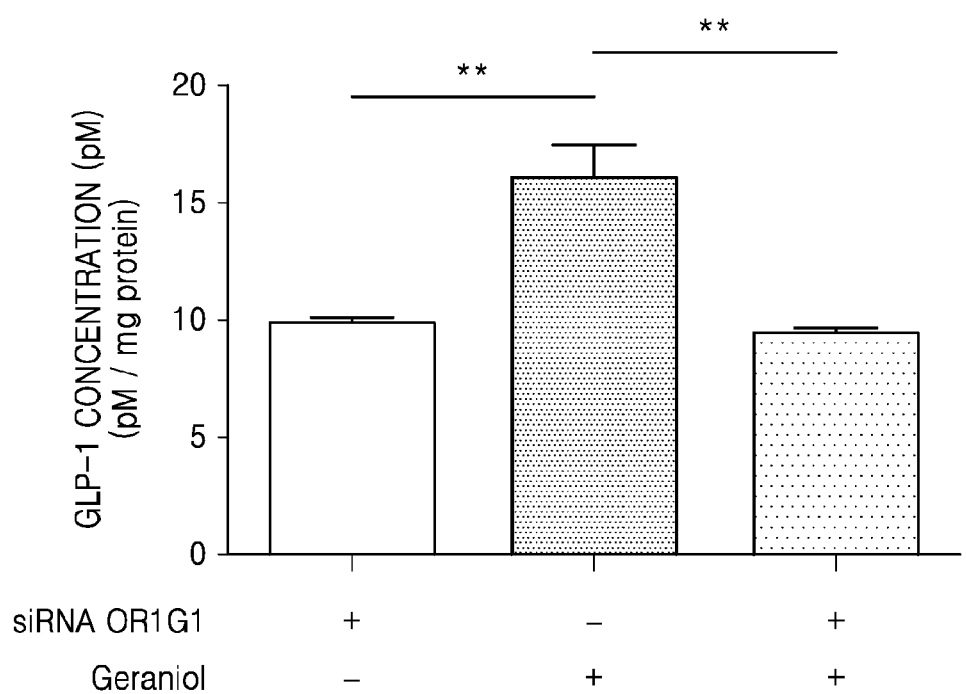
FIG. 1C is a graph showing that geraniol stimulates an olfactory receptor, OR1G1, promoting GLP-1 secretion.

The human enteroendocrine cells in which olfactory receptors were knocked-down and a normal human enteroendocrine cell were each treated with geraniol at a concentration of 100 μM. Then, the cells were cultured for 1 hour at 37° C. at a concentration of 5% $CO_2$. Thereafter, GLP-1 secretion was identified using ELISA. FIG. 1B is a graph showing that geraniol stimulates OR1A1, an olfactory receptor, promoting GLP-1 secretion. FIG. 1C is a graph showing that geraniol stimulates OR1G1, an olfactory receptor, promoting GLP-1 secretion. As shown in FIGS. 1B and 1C, it was found that geraniol stimulates olfactory receptors, such as OR1A1 and/or OR1G1, promoting GLP-1 secretion. Accordingly, it was found that the incretin hormone secretion mechanism of geraniol in a human enteroendocrine cell was through stimulation of olfactory receptors.

Figure 2:
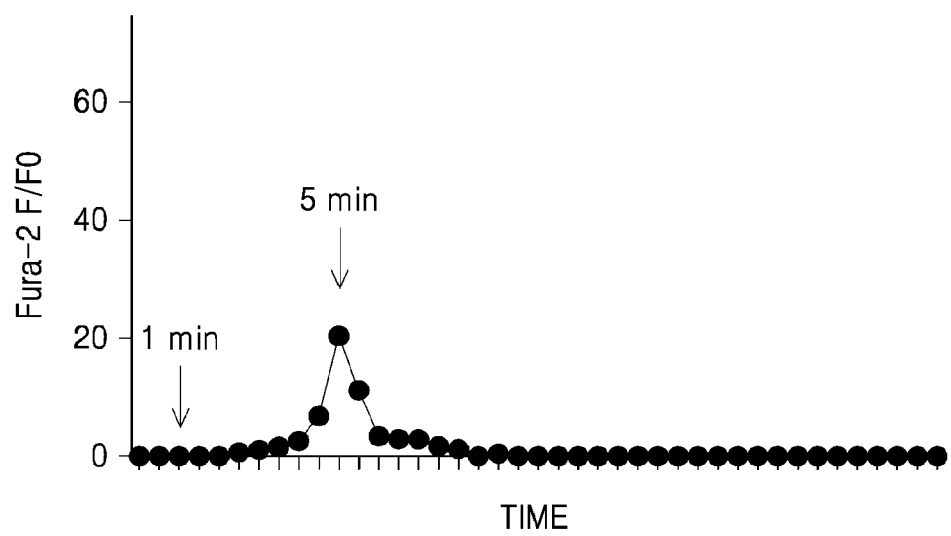
FIG. 2 is a graph showing change of calcium concentration in a human enteroendocrine cell after geraniol treatment. 100 μM of geraniol was treated after 1 minute elapsed from the start of the experiment, and the calcium concentration in the cell was found to be the highest after 4 minutes elapsed.

(3) Verification of Change Amount of Calcium Concentration in Human Enteroendocrine Cell after Geraniol Treatment FIG. 2 is a graph showing the change of calcium concentration in a human enteroendocrine cell after geraniol treatment. 100 μM of geraniol was treated after 1 minute elapsed from the start of the experiment, and the calcium concentration in the cell was found to be the highest after 4 minutes elapsed.

(4) Verification of Change Amount of cAMP after Geraniol Treatment

In a human enteroendocrine cell, the result of geraniol treatment (100 μM) and forskolin treatment (10 μM), which is a cAMP activator, were compared with each other. It was found that stimulation to olfactory receptors by geraniol was via cAMP activation in the GLP-1 secretion mechanism, and geraniol treatment had similar tendency with that of forskolin, which is a cAMP activator, by using cAMP ELISA, based on the user manual (Enzo Life Science, USA).

Figure 3:
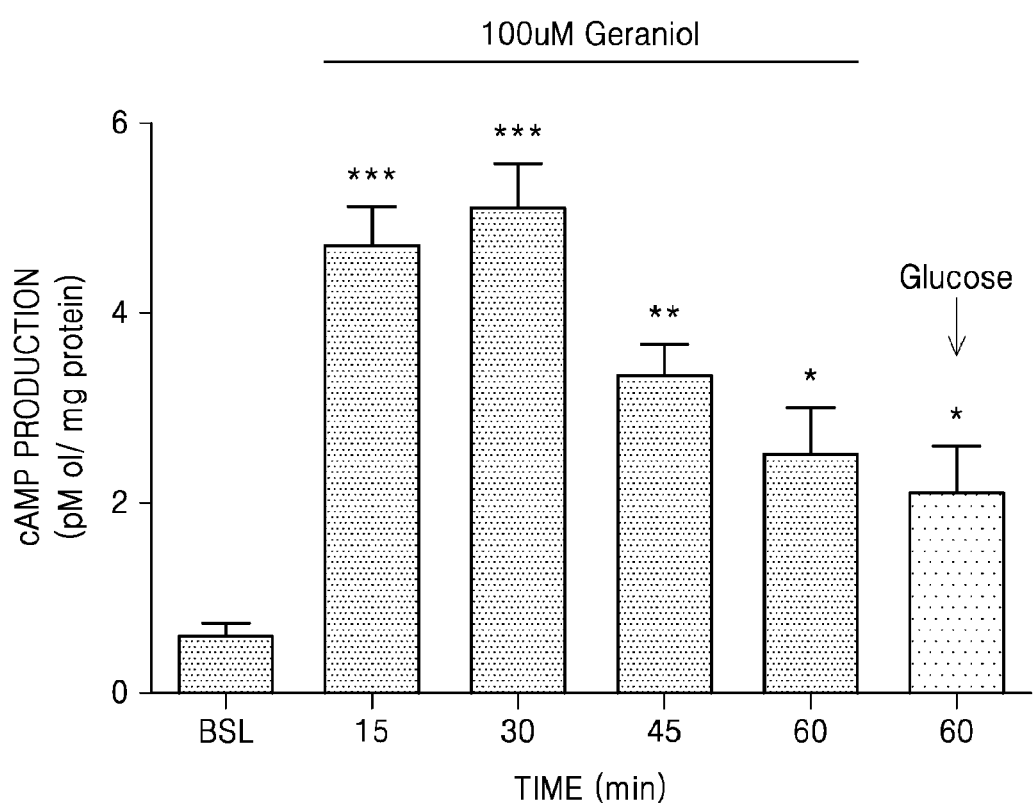
FIG. 3 is a graph of measurement of change amount of cAMP in a cell versus time after geraniol treatment. After 30 minutes elapsed from 100 μM geraniol treatment, the concentration of cAMP in the cell was the highest, and then decreased thereafter.

FIG. 3 is a graph of measurement of the change amount of cAMP in a cell versus time after geraniol treatment. As shown in FIG. 3, after 30 minutes elapsed from 100 μM geraniol treatment, the concentration of cAMP in the cell was the highest, and then decreased thereafter.

Figure 4:
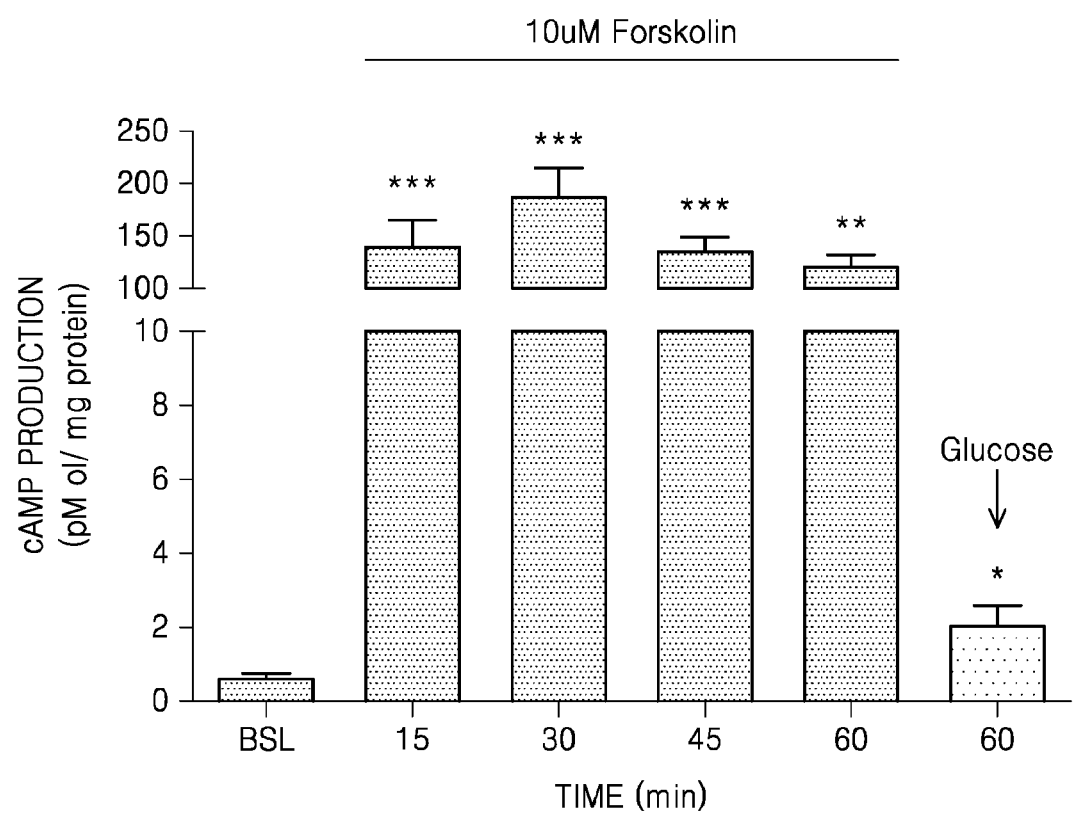
FIG. 4 is a graph of measurement of change amount of cAMP in a cell versus time after treatment of forskolin, which is a cAMP activator.

Furthermore, FIG. 4 is a graph of measurement of the change amount of cAMP in a cell versus time after treatment of forskolin, which is a cAPM activator. FIG. 4 is a graph of measurement of the change amount of cAMP after 10 minutes elapsed from 10 μM forskolin treatment. Forskolin treatment was found to show a similar pattern as the geraniol treatment.

(5) Verification of Presence of Olfactory Receptor in Small Intestine of Human and Mouse In order to identify the presence of an olfactory receptor in small intestine of human and mouse, immunofluorescent staining was carried out. The results thereof are shown in FIGS. 7A and 7B.

Figure 7A:
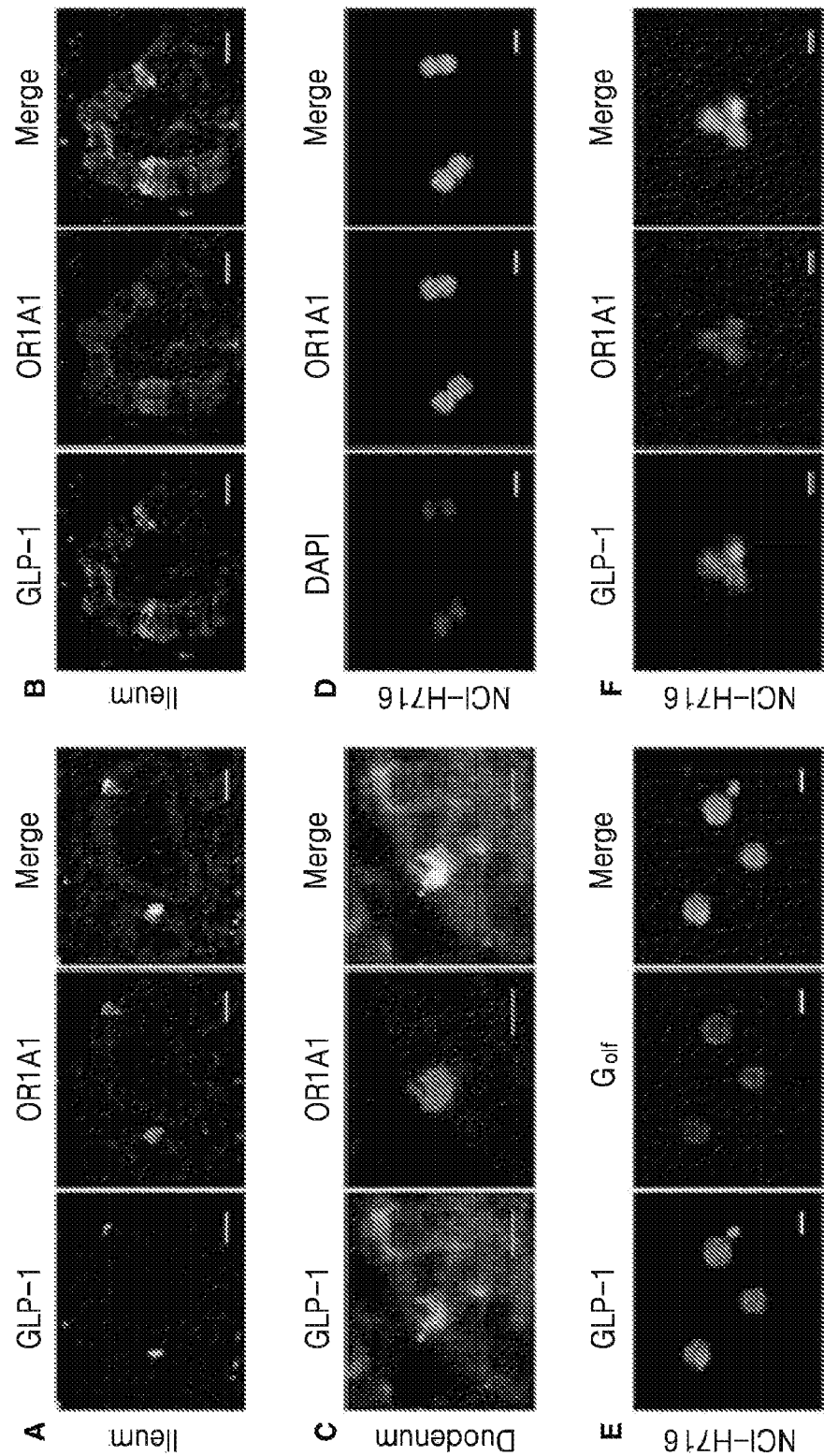
FIGS. 7A and 7B are images that verify the presence of olfactory receptors in the small intestine of human and mouse through immunofluorescent staining.
Figure 7B:
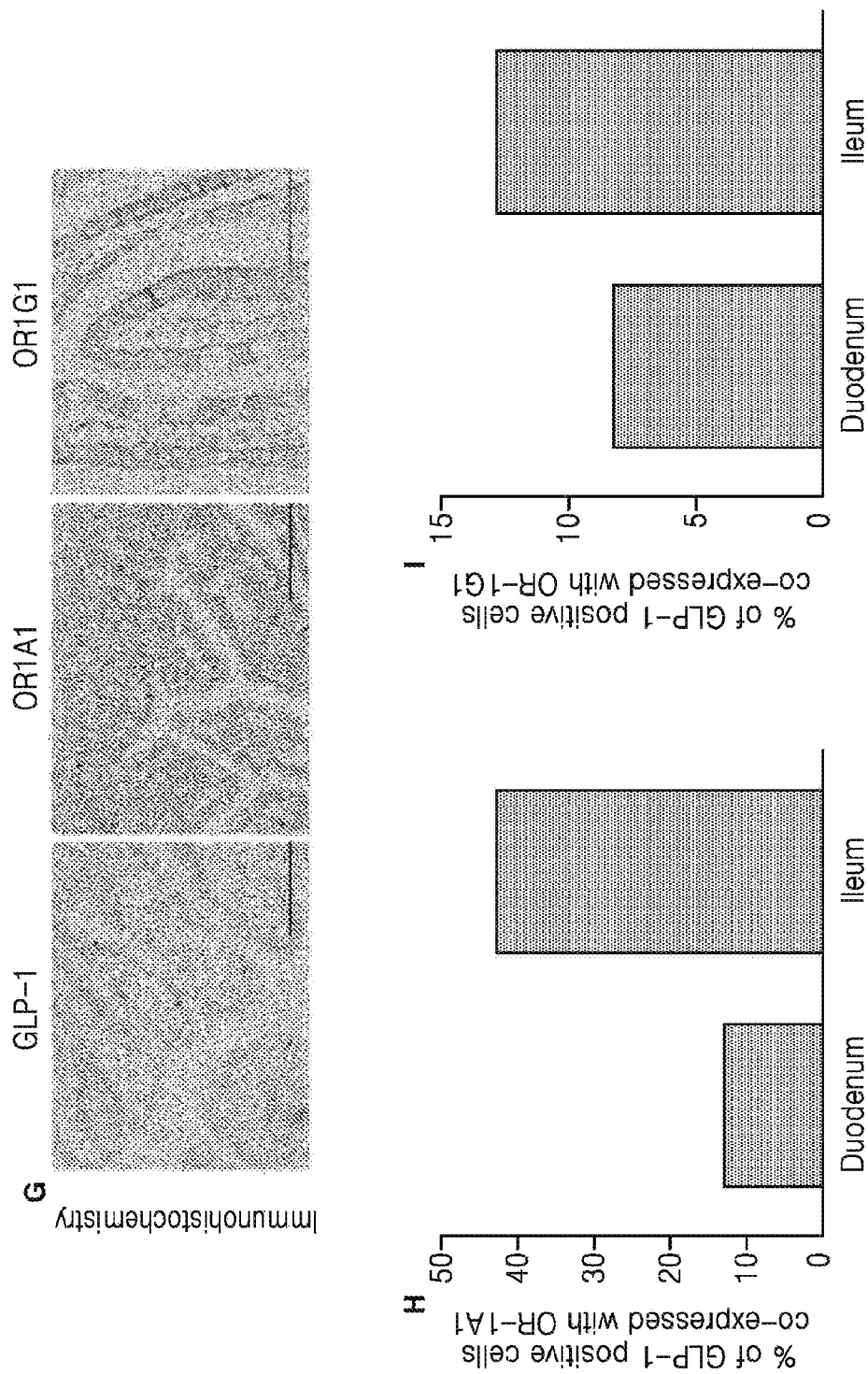

FIGS. 7A and 7B are images that verify the presence of olfactory receptors in the small intestine of human and mouse through immunofluorescent staining FIG. 7A A to C are results that verify GLP-1 co-expression with OR1A1 (olfactory receptor family 1 subfamily A member 1) or OR1G1 in an ileum tissue of a human through immunofluorescent staining. FIG. 7A D to F are results that verify expression of GLP-1 and OR1A1, OR1G1, or Golf (G protein, olfactory type) in an NCI-H716 cell, i.e., a human enteroendocrine cell.

FIG. 7B G to I are results that verify GLP-1 co-expression with olfactory marker protein (OMP), OR1G1, or OR1A1 in duodenum and small intestine tissues of a mouse. FIG. 7B H illustrates % of GLP-1 positive cells co-expressed with OR1A1. In FIG. 7B H, in an order from the left to the right, the graphs each indicate duodenum and ileum. It was found that the GLP-1 positive cells co-expressed with OR1A1 were found in a higher ratio in ileum than in duodenum. In addition, FIG. 7B I illustrates % of GLP-1 positive cells co-expressed with OR1G1. In FIG. 7B I, in an order from the left to the right, the graphs each indicate duodenum and ileum. It was found that the GLP-1 positive cells co-expressed with OR1A1 were found in a higher ratio in ileum than in duodenum.

EXAMPLE 2

Verification of Hypoglycemic Effect and GLP-1 and Insulin Secretion Effect in Mouse Model in the Case of Oral Administration of Geraniol (1) Hypoglycemic Effect in Mouse Model Oral glucose tolerance test was performed on a db/db mouse (leptin receptor knocked-out mice) (35 g to 39 g), which is a type II diabetes mellitus model. A male 6 week-old db/db mouse was purchased from Daehan Biolink Co., Ltd (DBL, South Korea).

A fasting blood sugar level of a db/db mouse of 18 hour-gastric emptying fasted state was measured. Then, the experimental group and the control group were each oral administered with geraniol and metformin, and saline via gavage. Geraniol was administered at 150 or 500 mg/weight Kg, and metformin was administered at 300 mg/weight Kg. Then, each group was administered with glucose of 5 g/weight Kg. Oral glucose tolerance test (OGTT) was performed after 10 minutes, 20 minutes, 40 minutes, 90 minutes, and 120 minutes elapsed. The results thereof are shown in FIG. 5A to 5C.

Figure 5A:
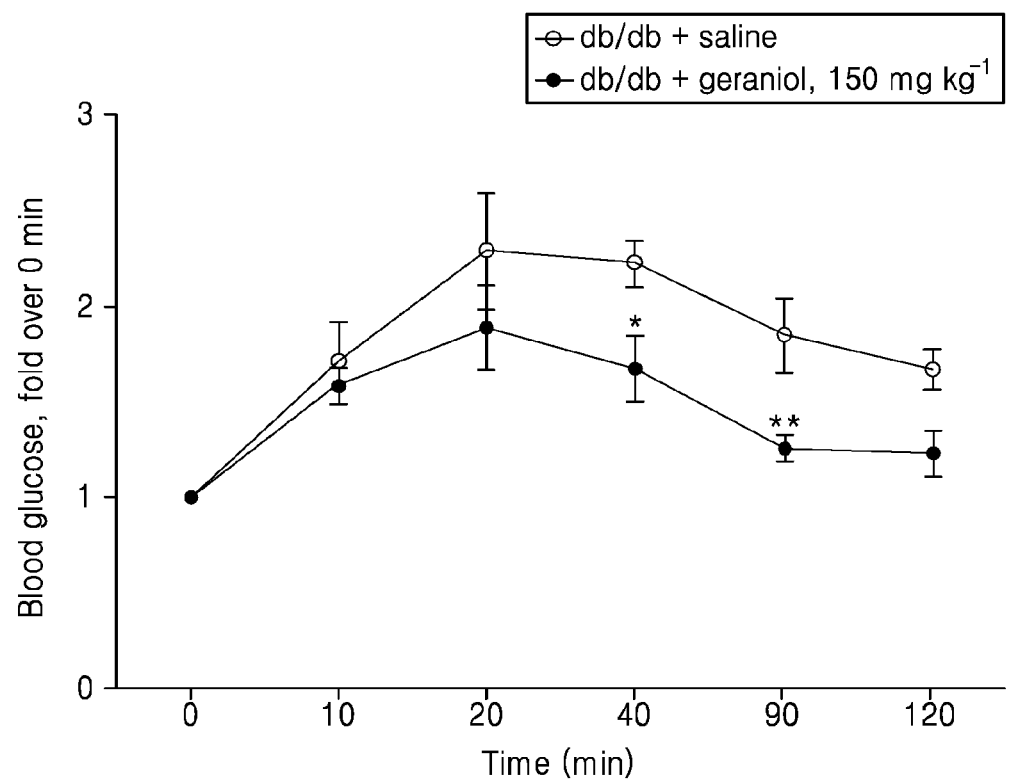
FIG. 5A is a graph of hypoglycemic effect in a type II diabetes mellitus mouse model at an oral glucose tolerance test, after gavage of geraniol of 150 mg/weight Kg.
Figure 5B:
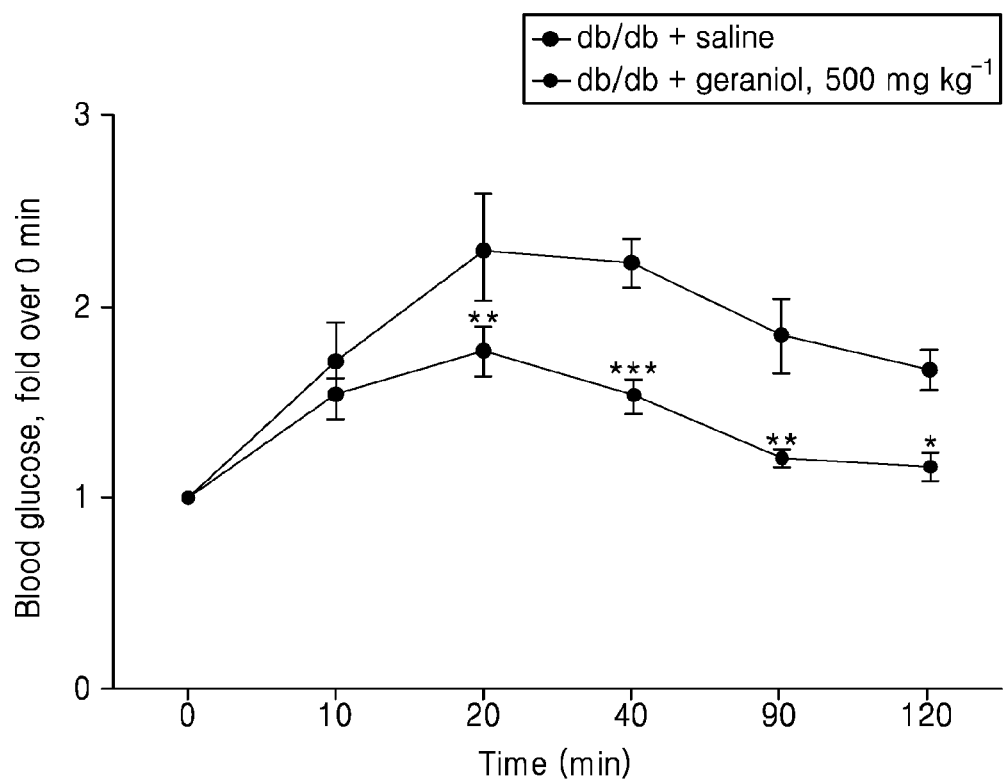
FIG. 5B is a graph of hypoglycemic effect in a type II diabetes mellitus mouse model at an oral glucose tolerance test, after gavage of geraniol of 500 mg/weight Kg.
Figure 5C:
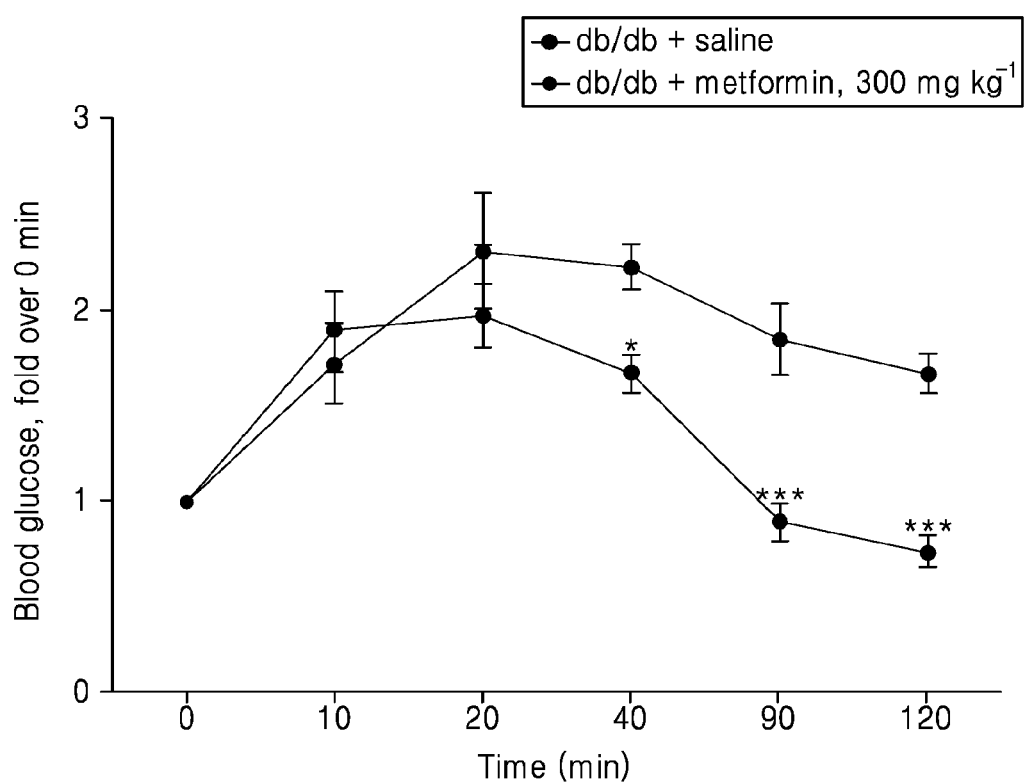
FIG. 5C is a graph of hypoglycemic effect in a type II diabetes mellitus mouse model at an oral glucose tolerance test, after gavage of metformin, which is used as an antidiabetic agent, of 300 mg/weight Kg. The effect thereof may be compared with that of geraniol.
Figure 6A:
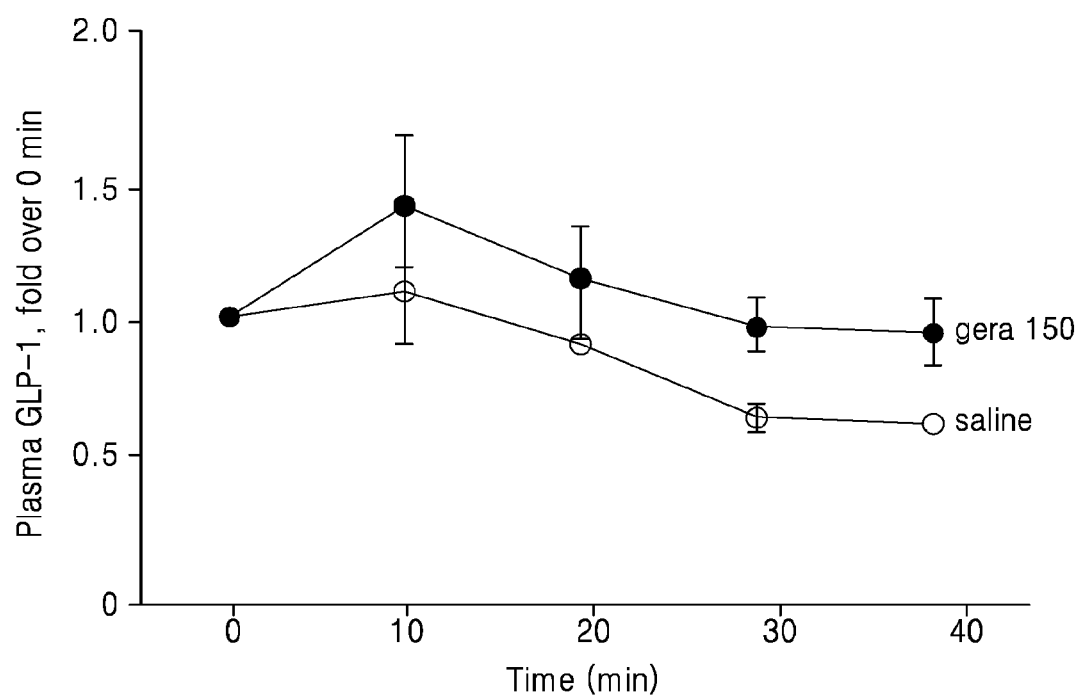
FIG. 6A is a graph of plasma GLP-1 increase effect in a type II diabetes mellitus mouse model at an oral glucose tolerance test, after gavage of geraniol of 150 mg/weight Kg.
Figure 6B:
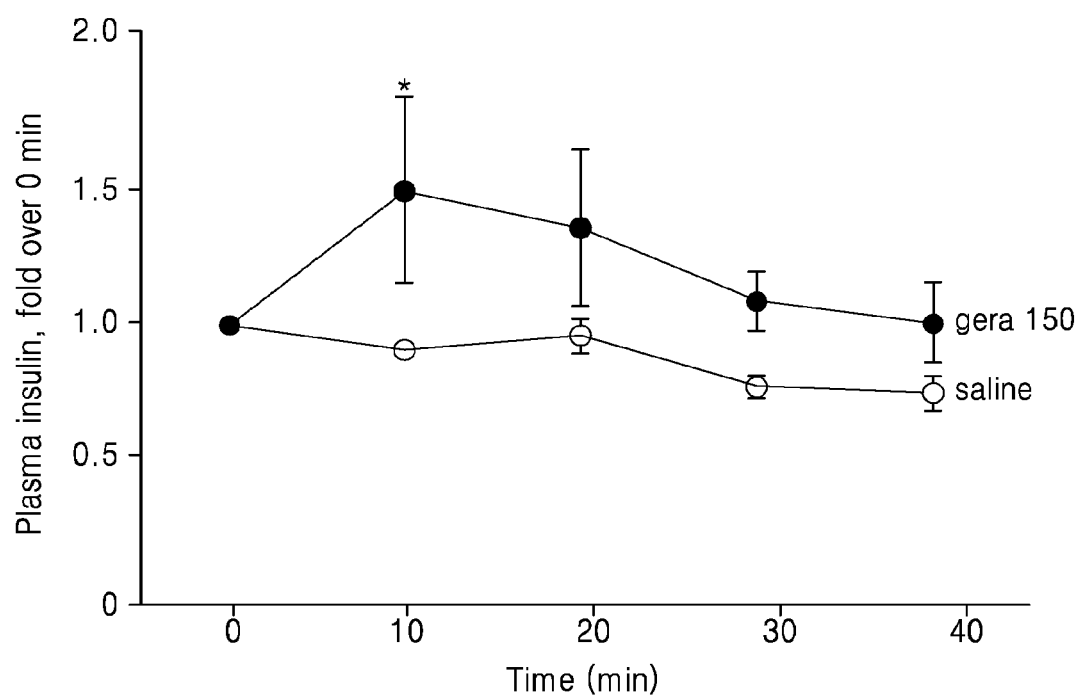
FIG. 6B is a graph of plasma insulin increase effect in a type II diabetes mellitus mouse model at an oral glucose tolerance test, after gavage of geraniol of 150 mg/weight Kg.
Figure 6C:
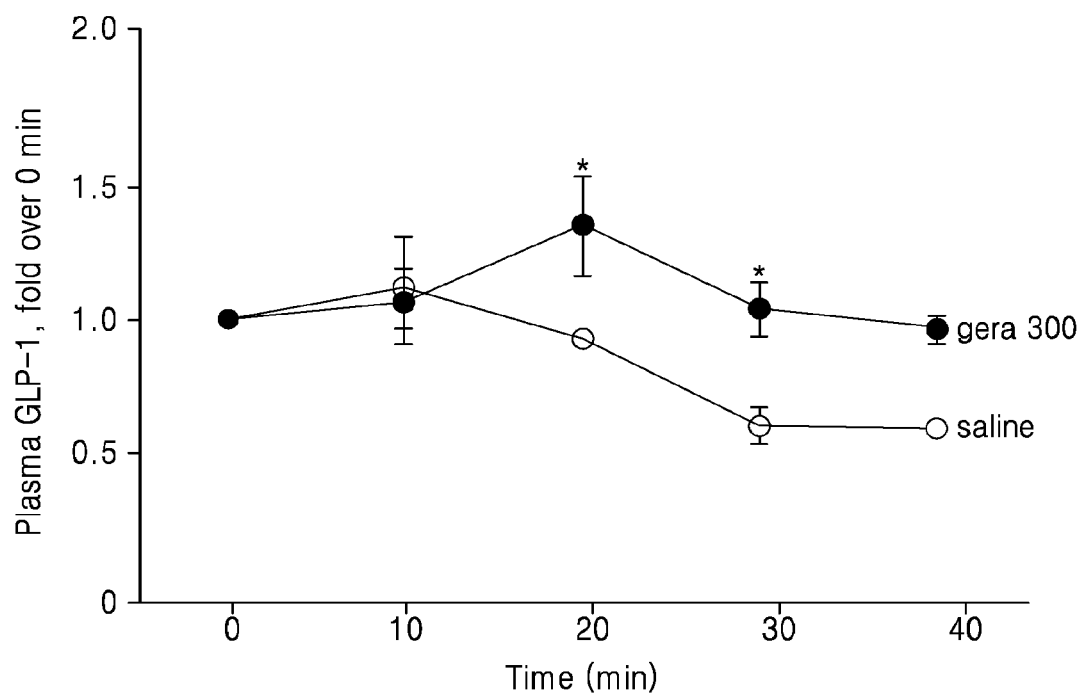
FIG. 6C is a graph of plasma GLP-1 increase effect in a type II diabetes mellitus mouse model at an oral glucose tolerance test, after gavage of geraniol of 300 mg/weight Kg.
Figure 6D:
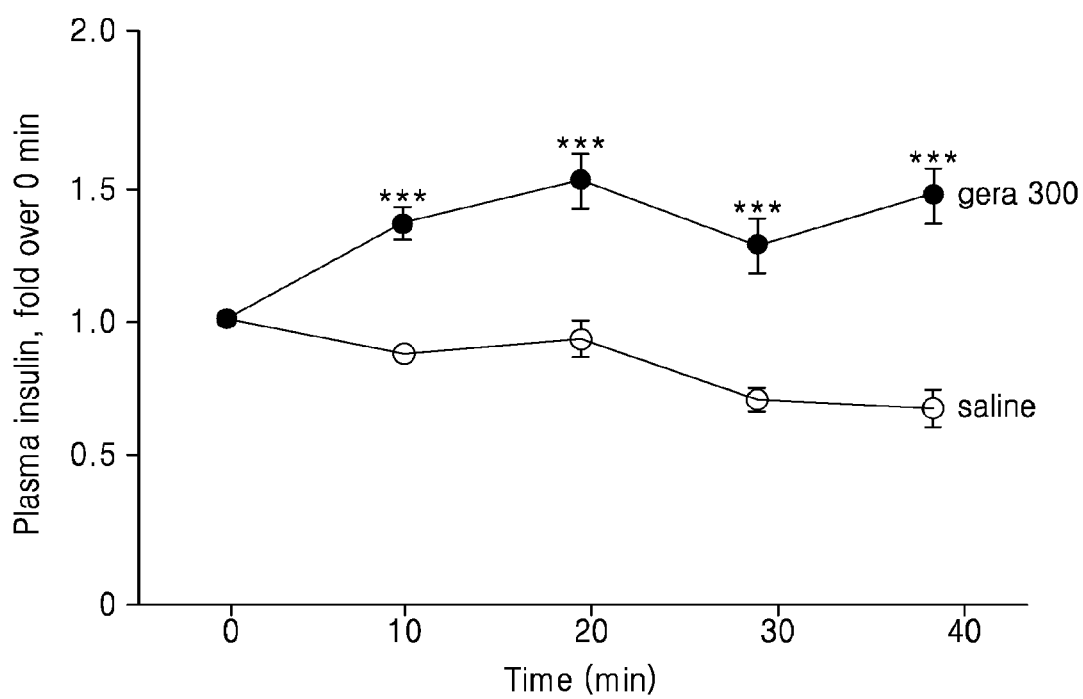
FIG. 6D is a graph of plasma insulin increase effect in a type II diabetes mellitus mouse model at an oral glucose tolerance test, after gavage of geraniol of 300 mg/weight Kg.

FIG. 5 are graphs of hypoglycemic effect in a type II diabetes mellitus mouse model in the case of oral administration of geraniol. As shown in FIGS. 5A to 5C, oral administration of geraniol exhibited hypoglycemic effect in a type II diabetes mellitus mouse model, as compared with the group administered with saline. Such hypoglycemic effect were found to be comparable to metformin, i.e., an antidiabetic agent.

(2) GLP-1 and Insulin Secretion Effect in Mouse Model

By using the same method in Example 2 (1), db/db mice of fasted state were each gavaged with geraniol, metformin, or saline. Then, each group were administered with glucose of 2 g/weight Kg. after 10 minutes, 20 minutes, 30 minutes, and 40 minutes elapsed, the amount of GLP-1 and insulin in plasma were measured by using multiplex assay (available from Bio-Rad, USA), based on the user manual, and Bio-Plex MAGPIX multiplex reader (available from Bio-Rad, USA). The results thereof are shown in FIGS. 6A to 6D.

FIGS. 6A to 6D are graphs of increase effect of GLP-1 and insulin in the plasma in a type II diabetes mellitus mouse model at an oral administration of geraniol. As shown in FIGS. 6A to 6D, in the case of oral administration of geraniol, hypoglycemic effect was found due to secretion inducing of GLP-1 and additional insulin, compared with a PBS administered group, in a type II diabetes mellitus mouse model. The effect was verified by comparing with metformin, i.e., an antidiabetic agent.

EXAMPLE 3

Verification of GLP-1 Secretion Promotion Effect and Hypoglycemic Effect in Diabetes Mellitus Mouse Model by Geraniol Smelling A male 6 week-old db/db mouse was purchased from Daehan Biolink Co., Ltd (DBL, South Korea). A fasting blood sugar level of a db/db mouse of 18 hour-gastric emptying fasted state was measured. Then, the experimental group was stimulated (smelling) with geraniol through olfaction. The control group was oral administered with saline and metformin of 300 mg/weight Kg via gavage. Then, each of the experimental group and the control group were administered with glucose of 2 g/weight Kg. After 10 minutes, 20 minutes, 40 minutes, 90 minutes, and 120 minutes elapsed, the amount of GLP-1 in plasma was verified by using multiplex assay (available from Bio-Rad, USA).

Figure 9:
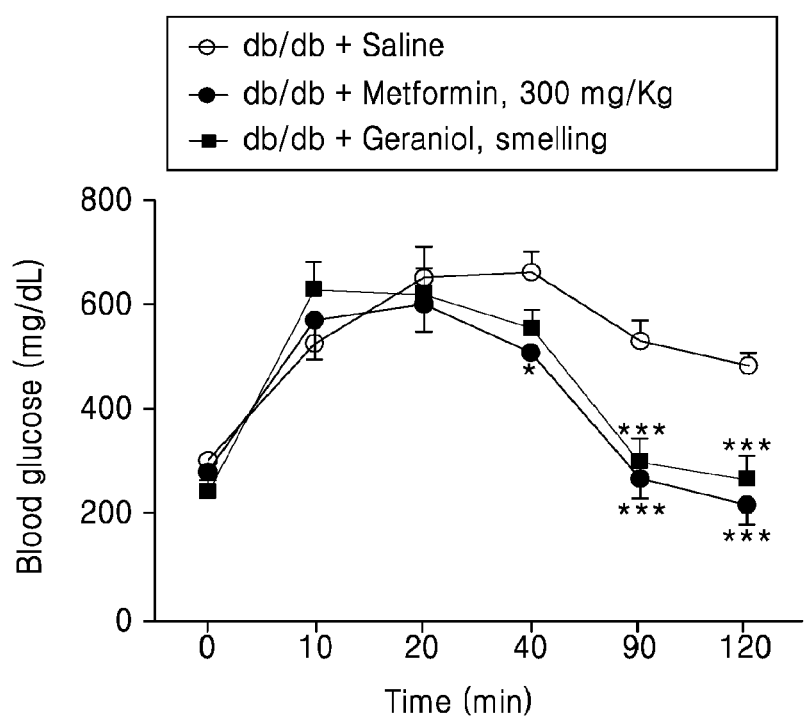
FIG. 9 is a graph of hypoglycemic effect in a type II diabetes mellitus mouse model at an oral glucose tolerance test, at an occurrence of smelling of geraniol. The graph shows a blood sugar level reducing due to geraniol olfactory stimulation, as compared with an oral glucose tolerance test of oral administration of metformin, i.e., an antidiabetic agent, at 300 mg/weight Kg, over time.

FIG. 9 is a graph of hypoglycemic effect over time for comparison between a group treated with geraniol and a group treated with PBS or metformin.

Figure 8:
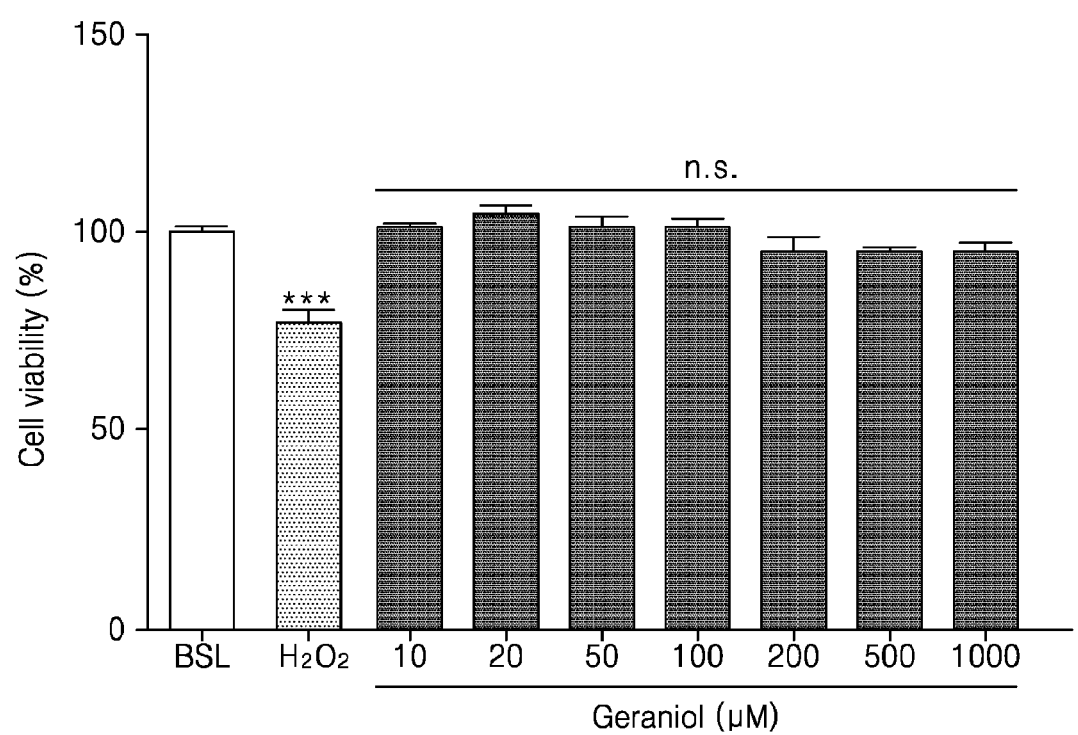
FIG. 8 is a graph for verifying cytotoxicity of geraniol in a human enteroendocrine cell through MTT assay. The results thereof are shown in cell viability (%) compared with a comparison group treated with PBS, and hydro peroxided ($H_2O_2$) was used as a positive control group. As a result, it was found that 10 to 1000 μM of geraniol had no cytotoxicity in an NCI-H716 cell, i.e., a human enteroendocrine cell.
Figure 10:
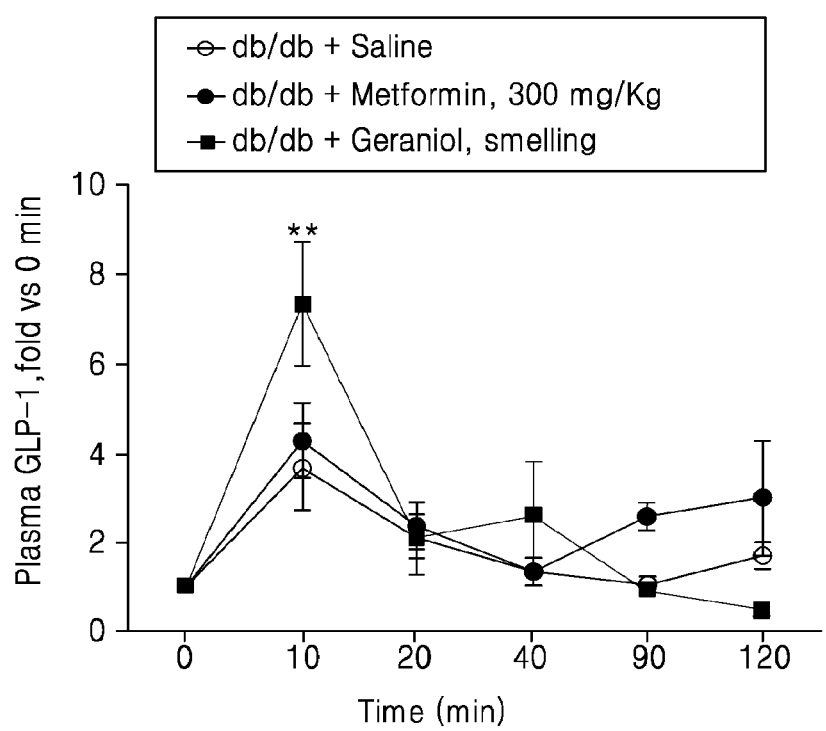
FIG. 10 is a graph of an increase of amount of GLP-1 in plasma of a type II diabetes mellitus mouse model at an oral glucose tolerance test, at an occurrence of smelling of geraniol. The graph shows a GLP-1 level increasing due to geraniol olfactory stimulation, as compared with an oral glucose tolerance test of oral administration of metformin, i.e., an antidiabetic agent, at 300 mg/weight Kg, over time.

FIG. 10 is a graph of the amount of GLP-1 over time for comparison between a group treated with geraniol and a group treated with PBS or metformin. As shown in FIG. 8, in the case of the experimental group of geraniol smelling, after 10 minutes elapsed from glucose administration, the amount of GLP-1 increased more than the case of metformin administration, increased to the maximum, and then decreased. From this fact, it was found that olfactory stimulation by geraniol lowered the blood sugar level by increasing the level of GLP-1 in the blood of a type II diabetes mellitus mouse. In addition, it was found that olfactory stimulation by geraniol has similar hypoglycemic effect as metformin, which is currently used as an antidiabetic agent by oral administration.

Conventional antidiabetic agents in the development field of a new treatment method with regard to diabetes mellitus have limitations in that the conventional antidiabetic agents cause side effects, such as liver dysfunction, hypoglycemia, or lacticacidemia. The present disclosure provides a novel method of screening a diabetes mellitus treat candidate material, based on the discovery of a mechanism, which is with regard to promotion of GLP-1 secretion through stimulating an olfactory receptor expressed in a human enteroendocrine cell or direct olfactory stimulation direc. It was found that geraniol screened by the screening method according to the present disclosure may stimulate an olfactory receptor in a human enteroendocrine cell, promoting GLP-1 secretion. In addition, hypoglycemic effect was found, which may be due to GLP-1 and insulin secretion through gavage and direct olfactory stimulation in a type II diabetes mellitus mouse model.

EXAMPLE 4

Cell Viability Assay of Geraniol

In order to verify cytotoxicity of geraniol on a human enteroendocrine cell, MTT assay was carried out as follows. In detail, cell viability assay was carried out using 3-(4,5-dimethylthiazol-2-yl)-2,5-diphenyltetrazolium) bromide (MTT) (available from Invitrogen, Carlsbad, Calif., USA). An endocrine cell, a NCI-H716 cell, was treated with geraniol of different levels of concentration and 6 mM MTT for 1 hour. Dimethyl sulfoxide (DMSO) was added to the cells, and absorbance thereof was measured using Bio-Rad model 680 microplated reader (Bio-Rad, Hercules, Calif., USA) at 540 nm.

FIG. 8 is a graph for verifying cytotoxicity of geraniol in a human enteroendocrine cell through MTT assay. The result thereof are shown in cell viability (%) compared with a comparison group treated with PBS, and hydro peroxided ($H_2O_2$) was used as a positive control group. As shown in FIG. 8, geraniol of 10 µM to 1000 µM, i.e., geraniol of 10 µM, 20 µM, 50 µM, 100 µM, 200 µM, 500 µM, and 1000 µM were found not to have cytotoxicity in a human enteroendocrine cell, i.e., a NCI-H716 cell.

Sequence Listing

Incorporation-By-Reference of Material Submitted Electronically

This application contains a sequence listing. It has been submitted electronically via EFS-Web as an ASCII text file entitled "PX047509_ST25.txt". The sequence listing is 1,268 bytes in size and was created on Jan. 25, 2016. Applicants state that (1) the computer readable form of the sequence listing submitted herewith is identical to the attached PDF copy; and (2) contains no new matter. It is hereby incorporated by reference in its entirety.

The invention claimed is:

1. A method of screening a test material to determine if the test material is a candidate for an antidiabetic agent for administration by inhalation, the method comprising:
   (a) contacting
      (i) an NCI-H716 cell, or a culture thereof, expressing human olfactory receptors OR1A1 and OR with the test material; and
      (ii) an NCI-H716 cell, or a culture thereof, for which the OR1A1 and/or OR1G1 expression has been knocked down with the test material;
   (b) measuring an expression level of glucagon-like peptide-1 (GLP-1) secreted from the NCI-H716 cell, or the culture thereof, of step (a)(i) expressing human olfactory receptors OR1A1 and OR1G1;
   (c) measuring an expression level of glucagon-like peptide-1 (GLP-1) secreted from the NCI-H716 cell, or the culture thereof, of step (a)(ii) for which the OR1A1 and/or OR1G1 expression has been knocked down; and
   (d) if the expression level of GLP-1 measured in the step (b) increases compared with before contacting with the test material, and
   the expression level of GLP-1 measured in the step (c) does not increase compared with before contacting with the test material,
   determining that the test material is a candidate material for an antidiabetic agent for administration by inhalation.

2. The method of claim 1, wherein the test material is an odorant.

3. The method of claim 2, wherein the odorant comprises a monoterpenoid.

4. The method of claim 2, wherein the odorant comprises geraniol.

5. The method of claim 1, wherein the contacting comprises incubating the NCI-H716 cell or the culture thereof, of step (a)(i) expressing human olfactory receptors OR1A1 and OR1G1, and the NCI-H716 cell, or the culture thereof, of step (a)(ii) for which the OR1A1 and/or OR1G1 expression has been knocked down with the test material at a concentration of 10 μM to 2000 μM.

6. The method of claim 1, wherein the measuring is identifying an increase of an amount of GLP-1 by an enzyme-linked immunosorbent assay (ELISA), a multiplex assay (GLP-1 multiplex assay), a radioimmunoassay, a quantitative immunofluorescence assay (fluorescent antibody method), or a latex agglutination assay.

* * * * *

SEQUENCE LISTING

<160> NUMBER OF SEQ ID NOS: 4

<210> SEQ ID NO 1

```
<211> LENGTH: 19
<212> TYPE: RNA
<213> ORGANISM: Artificial Sequence
<220> FEATURE:
<223> OTHER INFORMATION: sense sequences of OR1A1 siRNA

<400> SEQUENCE: 1
cugauguucg ccuucacaa                                            19

<210> SEQ ID NO 2
<211> LENGTH: 19
<212> TYPE: RNA
<213> ORGANISM: Artificial Sequence
<220> FEATURE:
<223> OTHER INFORMATION: antisense sequences of OR1A1 siRNA

<400> SEQUENCE: 2
uugugaaggc gaacaucag                                            19

<210> SEQ ID NO 3
<211> LENGTH: 19
<212> TYPE: RNA
<213> ORGANISM: Artificial Sequence
<220> FEATURE:
<223> OTHER INFORMATION: sense sequences of OR1G1 siRNA

<400> SEQUENCE: 3
cuccuacuca gggugucua                                            19

<210> SEQ ID NO 4
<211> LENGTH: 19
<212> TYPE: RNA
<213> ORGANISM: Artificial Sequence
<220> FEATURE:
<223> OTHER INFORMATION: antisense sequences of OR1G1 siRNA

<400> SEQUENCE: 4
uagacacccu gaguaggag                                            19
```